United States Patent
Ortiz et al.

(10) Patent No.: US 10,106,560 B2
(45) Date of Patent: Oct. 23, 2018

(54) PROCESS AND INTERMEDIATES FOR MAKING TUBULYSIN ANALOGS

(71) Applicant: BRISTOL-MYERS SQUIBB COMPANY, Princeton, NJ (US)

(72) Inventors: Adrian Ortiz, Belle Meade, NJ (US); Carlos A. Guerrero, Plainsboro, NJ (US); Bin Zheng, Kendall Park, NJ (US); Jason J. Zhu, East Brunswick, NJ (US); Michael Anthony Schmidt, Woodbridge, NJ (US); Michael R. Luzung, Jersey City, NJ (US); Martin D. Eastgate, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/623,570

(22) Filed: Jun. 15, 2017

(65) Prior Publication Data

US 2017/0362259 A1  Dec. 21, 2017

Related U.S. Application Data

(60) Provisional application No. 62/350,840, filed on Jun. 16, 2016.

(51) Int. Cl.
| | | |
|---|---|---|
| *C07D 417/12* | (2006.01) | |
| *C07F 7/18* | (2006.01) | |
| *C07D 211/28* | (2006.01) | |
| *C07F 7/08* | (2006.01) | |

(52) U.S. Cl.
CPC .......... *C07F 7/1856* (2013.01); *C07D 211/28* (2013.01); *C07D 417/12* (2013.01); *C07F 7/0818* (2013.01); *C07F 7/1852* (2013.01)

(58) Field of Classification Search
None
See application file for complete search history.

(56) References Cited

U.S. PATENT DOCUMENTS

| | | |
|---|---|---|
| 7,816,377 B2 | 10/2010 | Domling et al. |
| 8,394,922 B2 | 3/2013 | Cheng et al. |
| 8,580,820 B2 | 11/2013 | Zanda et al. |
| 8,980,824 B2 | 3/2015 | Cong et al. |
| 8,980,833 B2 | 3/2015 | Richter et al. |
| 2010/0047841 A1 | 2/2010 | Wipf et al. |
| 2016/0130299 A1 | 5/2016 | Perez et al. |

FOREIGN PATENT DOCUMENTS

WO    WO 2009/134279 A1    11/2009

OTHER PUBLICATIONS

Colombo, R. et al., J. Org. Chem. 2016 vol. 81 pp. 10302-10320.*
Hamel, et al., "Antimitotic Peptide and Depsipeptides," *Curr. Med. Chem. Anti-Cancer Agents*, vol. 2, pp. 19-53, 2002.
Kazmaier, et al., "Synthetic Approaches Towards Tubulysins and Derivatives Thereof," *Open Natural Products Journal*, vol. 6, pp. 12-30, 2013.
Khalil, et al., "Mechanism of Action of Tubulysin, an Antimitotic Peptide from Myxobacteria," *ChemBioChem*, vol. 7: pp. 678-683, 2006.
Kwon, et al., "Synthesis of Bicyclic Guanidines via Cascade Hydroamination/ Michael Additions . . . ," *Organic Letters*, vol. 16, No. 23, pp. 6048-6051, 2014.
Li, et al., "AlMe₃-Promoted Formation of Amides from Acids and Amines," *Organic Letters* vol. 14 No. 1, pp. 214-217, 2012.
Lipshutz, et al., "Synthesis of Activated Alkenylboronates from Acetylenic Esters . . . ," *Angewandte Chemie*, vol. 47, pp. 10183-10186, 2008.
Park, et al., "Synthesis of a Cyclic Analogue of Tuv N-Methyl Tubulysin," *Syn Lett*, vol. 26, pp. 1063-1068, 2015.
Rooke, et al., "Stereoselective Syntheses of Trisubstituted Olefins via Platinum Catalysis: . . . ," *J. AM CHEM*, vol. 132, pp. 11926-11928, 2010.
Rooke, et al., "Palladium-Catalyzed Hiyama Couplings of . . . ," *Organic Letters*, vol. 14, No. 13, pp. 3328-3331, 2012.
Rooke, et al., "An Analysis of the Influences Dictating Regioselectivity in Platinum-Catalyzed Hydrosilylations of Internal Alkynes," *Tetrahedron*, vol. 70, pp. 4232-4244, 2014.
Sani, et al., "Total Synthesis of Tubulysins U and V**," *Angew. Chem. Int.*, vol. 46, pp. 3526-3529, 2007.
Schrama, et al., "Antibody Targeted Drugs as Cancer Therapeutics," *Nature Reviews Drug Discovery*, vol. 5, pp. 147-159, 2006.
Shi, et al., "Copper-Catalysed Selective Hydroamination Reactions of Alkynes," *Nature Chemistry*, vol. 7, pp. 38-45, 2015.
Shibue, et al., "Total Syntheses of Tubulysins," *Chem. Eur.*, vol. 16, pp. 11678-11688, 2010.
Sumida, et al., "Palladium-Catalyzed Regio-and Stereosleective Hydrosilylation of Electron-Deficient Alkynes," *Organic Letters*, vol. 14, No. 6, pp. 1552-1555, 2012.

(Continued)

*Primary Examiner* — Heidi Reese
(74) *Attorney, Agent, or Firm* — Yuan Chao

(57) ABSTRACT

An improved process for making a compound B of the structure

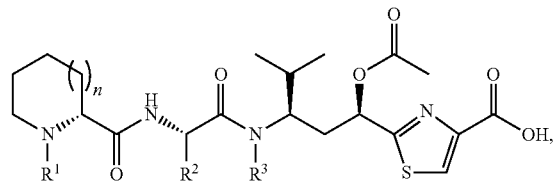

B wherein n, $R^1$, $R^2$, and $R^3$ are as defined in the specification. Compound B can be used to make tubulysin analogs that are, in turn, useful as anti-cancer agents, particularly when deployed in an antibody-drug conjugate.

16 Claims, 6 Drawing Sheets

(56) References Cited

OTHER PUBLICATIONS

Yang, et al., "Total Synthesis of Tubulysin U and its C-4 Epimer," *Chem. Asian Journal.*, vol. 8, pp. 1213-1222, 2013.
International Search Report and Written Opinion, for PCT Application No. PCT/US2017/037588, dated Sep. 15, 2017.

\* cited by examiner

PROCESS AND INTERMEDIATES FOR MAKING TUBULYSIN ANALOGS

CROSS-REFERENCE TO RELATED APPLICATIONS

This application claims the benefit under 35 U.S.C. § 119(e) of U.S. Provisional Application Ser. No. 62/350,840, filed Jun. 16, 2016; the disclosure of which is incorporated herein by reference.

BACKGROUND OF THE INVENTION

This application relates to a process for making tubulysin analogs, especially those adapted for making antibody-drug conjugates, and intermediates used in such process.

The tubulysins are cytotoxins first isolated from cultures of the myxobacteria *Archangium gephyra* or *Angiococcus disciformis*, each producing a different tubulysin mixture. They belong to a group of antimitotic polypeptides and depsipeptides that includes the phomopsins, the dolastatins, and the cryptophycins (Hamel 2002). During mitosis, a cell's microtubules reorganize to form the mitotic spindle, a process requiring the rapid assembly and disassembly of the microtubule constituent proteins α- and β-tubulin. Antimitotic agents block this process and prevent a cell from undergoing mitosis. At the molecular level the exact blockage mechanism may differ from one antimitotic agent to another. The tubulysins prevent the assembly of the tubulins into microtubules, causing the affected cells to accumulate in the $G_2/M$ phase and undergo apoptosis (Khalil et al. 2006). (Full citations for the documents cited herein by first author or inventor and year are listed at the end of this specification.)

The tubulysins have a tetrapeptidyl scaffold consisting of one proteinogenic and three non-proteinogenic amino acid subunits as shown in formula (I): N-methylpipecolinic acid (Mep), isoleucine (Ile), tubuvaline (Tuv), and either tubuphenylalanine (Tup, R' equals H) or tubutyrosine (Tut, R' equals OH). The tubulysins are named A, B, and so forth, with structural variations at residues R', R" and R'" of formula (I) as shown in Table I.

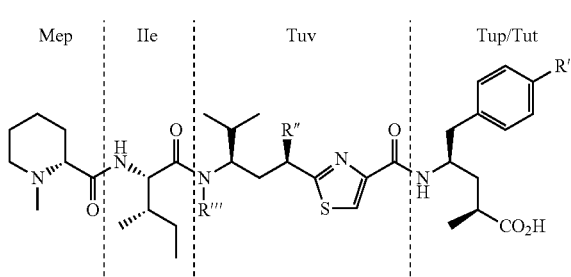

(I)

TABLE I

Naturally Occurring Tubulysins

| Tubulysin | R' | R" | R'" |
|---|---|---|---|
| A | OH | OC(=O)Me | CH$_2$OC(=O)i-Bu |
| B | OH | OC(=O)Me | CH$_2$OC(=O)n-Pr |
| C | OH | OC(=O)Me | CH$_2$OC(=O)Et |
| D | H | OC(=O)Me | CH$_2$OC(=O)i-Bu |
| E | H | OC(=O)Me | CH$_2$OC(=O)n-Pr |
| F | H | OC(=O)Me | CH$_2$OC(=O)Et |
| G | OH | OC(=O)Me | CH$_2$OC(=O)CH=CH$_2$ |
| H | H | OC(=O)Me | CH$_2$OC(=O)Me |
| I | OH | OC(=O)Me | CH$_2$OC(=O)Me |
| U | H | OC(=O)Me | H |
| V | H | OH | H |
| Y | OH | OC(=O)Me | H |
| Z | OH | OH | H |
| Pretubulysin | H | H | Me |

The potency of the tubulysins has engendered substantial interest in using them or their analogs as anticancer agents. Consequently, there exists substantial art on the synthesis of the tubulysins or their analogs. See, for example: Cheng et al. 2013; Cong et al. 2015; Domling et al. 2010; Kazmaier et al. 2013; Park et al. 2015; Perez et al. 2015; Richter 2015; Sani et al. 2007; Shibue et al. 2010; Wipf et al. 2010; Yang et al. 2013; and Zanda et al. 2013.

A type of anticancer agent that is generating strong interest is an antibody-drug conjugate (ADC, also referred to as an immunoconjugate). In an ADC, a therapeutic agent (also referred to as the drug, payload, or warhead) is covalently linked via a linker to an antibody whose antigen is expressed by a cancer cell (tumor associated antigen). The antibody, by binding to the antigen, delivers the ADC to the cancer site. There, cleavage of the linker or degradation of the antibody leads to the release of the therapeutic agent. Conversely, while the ADC is circulating in the blood system, the therapeutic agent is held inactive because of its covalent linkage to the antibody. Thus, the therapeutic agent used in an ADC can be much more potent (i.e., cytotoxic) than ordinary chemotherapy agents because of its localized release. For a review on ADCs, see Schrama et al. 2006.

Tubulysin analogs have been proposed as the therapeutic agent in an ADC. For such use, it is necessary that a tubulysin analog have a functional group suitable for attachment of the linker. While the carboxyl group in the Tup subunit or the phenolic hydroxyl in tubulysin A can in principle serve as such functional group, a preferred functional group is a primary amine (—NH$_2$) group, so that the linker can be attached via enzymatically cleavable peptidyl bonds. As the naturally occurring tubulysins lack a primary amine group, analogs have been made introducing such a group, especially at the 4-position of the Tup subunit. See Cheng et al. 2013; Cong et al. 2015; and Perez et al. 2015. Some of these analogs can be represented by the generic formula below, where n is 0, 1, or 2 and $R^a$, $R^b$, $R^c$, $R^d$, and $R^e$ represent either residues found in the naturally occurring tubulysins or variants thereof:

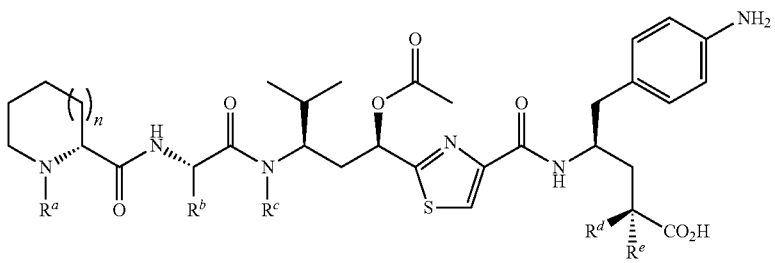

Tubulysin Analog with 4-NH$_2$ group in Tup subunit

Attachment of a linker to the above analog provides a tubulysin analog/linker compound having a structure represented by formula A:

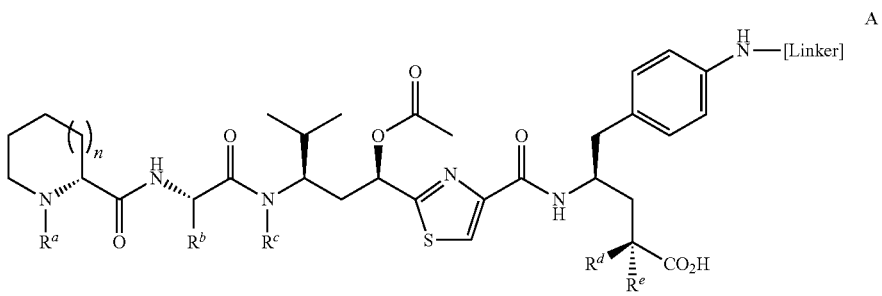

Conjugation to an antibody provides an ADC, represented by the formula below. The number of tubulysin analog molecules attached to each antibody—the drug-antibody ratio, or DAR—will depend on the conjugation chemistry, the structure of the antibody, and the structure of the linker. In the formula below, a DAR of 1 is shown for simplicity.

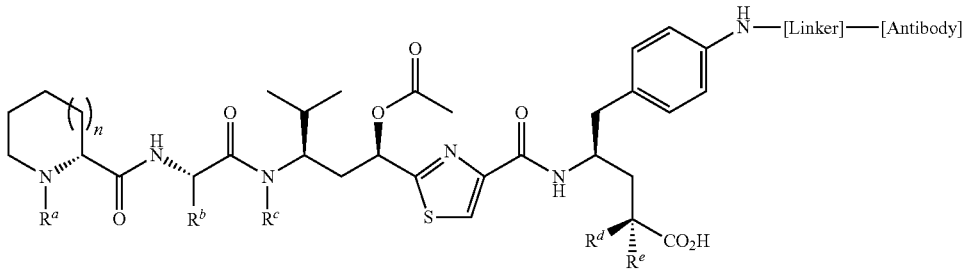

Antibody-Drug Conjugate with Tubulysin Analog as Payload

A key synthetic challenge to the preparation of such an ADC lies in the making of analog/linker A. Cheng et al. 2013 disclose a scheme entailing the coupling of a fragment B comprising the Mep, Ile, and Tuv subunits and a fragment C comprising the amine-modified Tup subunit and the linker to prepare an analog/linker A.

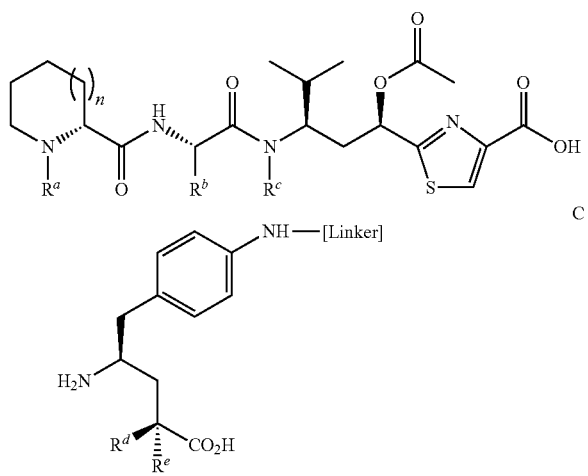

A specific analog/linker made by Cheng et al. 2013 is A1, whose structure is shown below. The scheme employed is recapitulated in FIGS. 1A-1B, with fragments B1 and C1 being exemplars of fragments B and C.

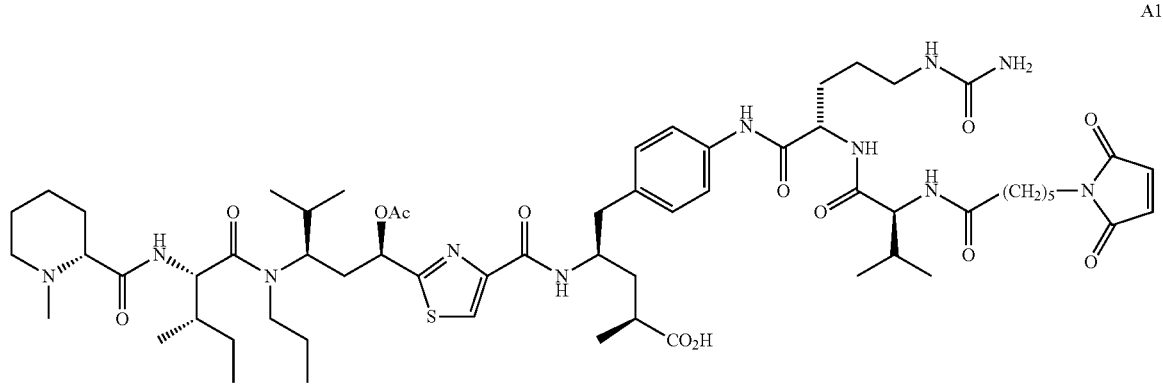

As can be seen from FIGS. 1A-1B, the synthesis of fragment B1 is highly linear, comprising over 12 steps, resulting in a low overall yield (estimated as 0.81% from compound 1 to compound B1 according to yields reported in Cheng et al. 2013). Further, azide 13 is potentially unstable and explosive, limiting the scheme's scalability due to safety considerations.

Thus, there is a need for a more efficient synthesis of analog/linkers A and, in particular, of fragment B, suitable for large-scale production.

BRIEF SUMMARY OF THE INVENTION

This invention provides an improved process for making fragment B and analog/linker A. The process is generally depicted in FIG. 2.

At each occurrence thereof, the elements in the structural formulae in FIG. 2 and in this application have the following meanings, unless the context indicates a narrower, preferred meaning is applicable:

n is 0, 1, or 2;
$R^0$ is $C_1$-$C_4$ alkyl (preferably t-butyl);
$R^1$ is H or $C_1$-$C_4$ alkyl;
$R^2$ is Me, Et, n-Pr, i-Pr, or (S) sec-butyl;
$R^3$ is Me, Et, or n-Pr;
$X^1$ is Cl, Br, I, triflate, mesylate, or tosylate;
$X^2$ is $C_1$-$C_3$ alkyl, aryl or benzyl; the aryl or benzyl group being optionally substituted with Cl, Br, Me, Et, CN, $NO_2$ or $O(C_1$-$C_3$ alkyl);
PG is a silyl protective group; and
LG is a leaving group.

The process shown in FIG. 2 is characterized by several unique steps and intermediates, which contribute to the reduction in the overall number of steps needed to arrive at fragment B and analog/linker A and an increase in overall yield, to the vicinity of 10%.

In a first aspect, this invention provides a process for making a compound 21, or a salt thereof,

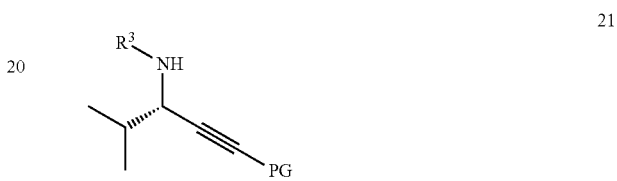

comprising the steps of
(a) combining a compound 18

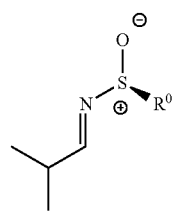

with a compound 19

Li—≡—PG   19 in a reaction medium and allowing the two compounds to react with each other;
(b) then adding to the reaction medium a compound 20

$R^3$—$X^1$   20

(c) then adding a de-chelating agent to the reaction medium to produce a compound 21; and (d) optionally adding a primary or secondary alcohol and an anion source to the reaction medium to produce a salt of compound 21.

In a second aspect, this invention provides a process for making a compound 23

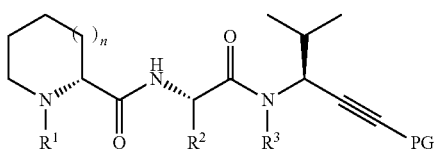

23 comprising reacting a compound 21

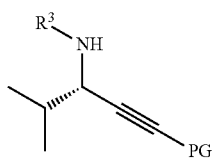

with a compound 22

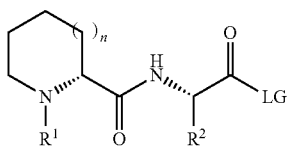

22 in the presence of a haloalkyl aluminum compound to form compound 23.

In a third aspect, this invention provides a process for making a compound 26

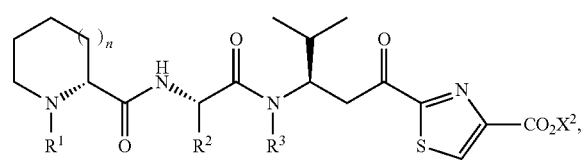

26 by regioselectively hydrating compound 25

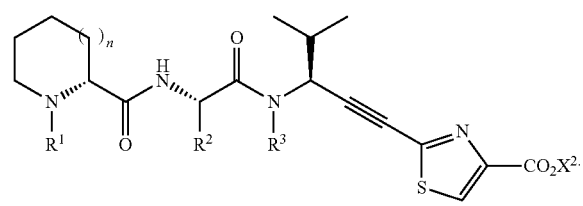

25

Preferably, the regioselective hydration of compound 25 comprises the steps of (a) treating compound 25 with a silicon or boron metalating agent in the presence of a metal catalyst selected from the group consisting of Pd, Pt, Cu, Ru, Rh and Au, to produce a metalated intermediate; and (b) oxidizing the metalated intermediate with an oxidizing agent to produce compound 26.

In fourth aspect, this invention provides a process for making a compound 27

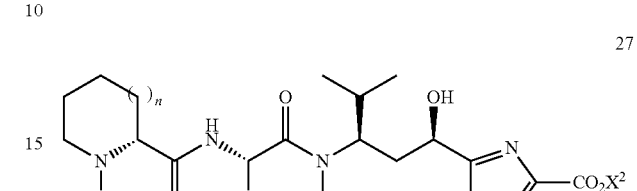

27 comprising the step of enantioselectively hydrogenating a compound 26

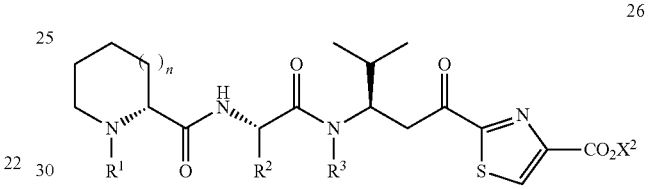

26 in the presence of an asymmetric hydrogenation catalyst, (preferably an R,R-Noyori catalyst).

In a fifth aspect, this invention provides a compound having a structure according to formula 21a″

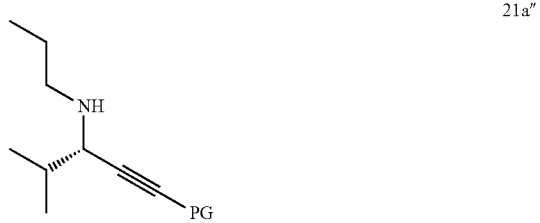

21a″ wherein PG is a silyl protecting group, preferably trimethyl silyl, triethyl silyl, triisopropyl silyl (more preferably), t-butyldiphenyl silyl, or t-butyldimethyl silyl; or a salt thereof.

In a sixth aspect, this invention provides a compound having a structure according to formula 23a

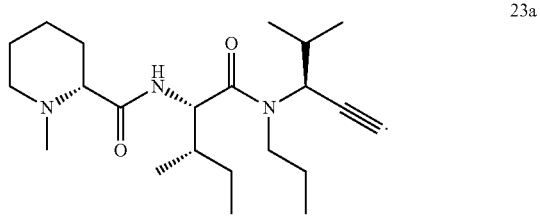 [SMILES: C#C[C@H](C(C)C)N(CCC)C(=O)[C@@H](NC(=O)[C@H]1CCCCN1C)[C@@H](C)CC]

23a

In a seventh aspect, this invention provides a compound having a structure according to formula 25

25

[Structure 25: piperidine-N(R¹)-C(O)-NH-CH(R²)-C(O)-N(R³)-CH(iPr)-C≡C-thiazole-CO₂X²]

wherein variables are as defined at the beginning of this section, but preferably are as follows: n is 1, $R^1$ is Me, $R^2$ is (S) sec-butyl, $R^3$ is n-Pr, and $X^2$ is $C_1$-$C_3$ alkyl.

In an eighth aspect, this invention provides a compound having a structure according to formula 26

26

[Structure 26: similar to 25 but with CH₂-C(O) in place of C≡C]

wherein variables are as defined at the beginning of this section, but preferably are as follows: n is 1, $R^1$ is Me, $R^2$ is (S) sec-butyl, $R^3$ is n-Pr, and $X^2$ is $C_1$-$C_3$ alkyl.

In a ninth aspect, this invention provides a process for making a compound B,

B

[Structure B: piperidine-N(R¹)-C(O)-NH-CH(R²)-C(O)-N(R³)-CH(iPr)-CH₂-CH(OAc)-thiazole-CO₂H]

comprising the steps of:
(a) preparing a compound 21 or a salt thereof

21

[Structure 21: R³-NH-CH(iPr)-C≡C-PG]

from compounds 18, 19 and 20

18

[Structure 18: iBu-CH=N-S(=O)(⊕)-R⁰ sulfinyl imine]

19

Li——≡——PG

20

$R^3$—$X^1$;

(b) reacting compound 21 with a compound 22

22

[Structure 22: piperidine-N(R¹)-C(O)-NH-CH(R²)-C(O)-LG]

in the presence of a haloalkyl aluminum compound to produce compound 23

23

[Structure 23: piperidine-N(R¹)-C(O)-NH-CH(R²)-C(O)-N(R³)-CH(iPr)-C≡C-PG]

(c) removing the group PG from compound 23 to form a compound 23'

23'

[Structure 23': same as 23 but with terminal alkyne H instead of PG]

(d) coupling compound 23' and a compound 24

24

[Structure 24: Hal-thiazole-CO₂X²]

to produce compound 25

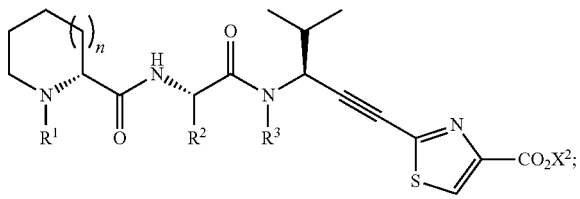

(e) regioselectively hydrating compound 25 to produce a compound 26

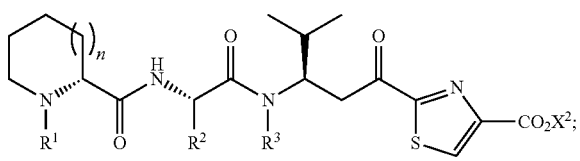

(f) enantioselectively reducing compound 26 to produce a compound 27

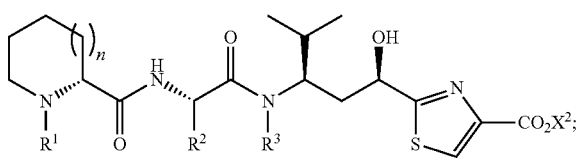

and (g) hydrolyzing the ester group and acetylating the hydroxyl group in compound 27 to produce compound B.

BRIEF DESCRIPTION OF THE DRAWING(S)

FIGS. 1A and 1B recapitulate, in combination, a scheme disclosed in Cheng et al. 2013 for the synthesis of analog/linker A1 from fragments B1 and C1.

DETAILED DESCRIPTION OF THE INVENTION

Definitions

Figure 1A:
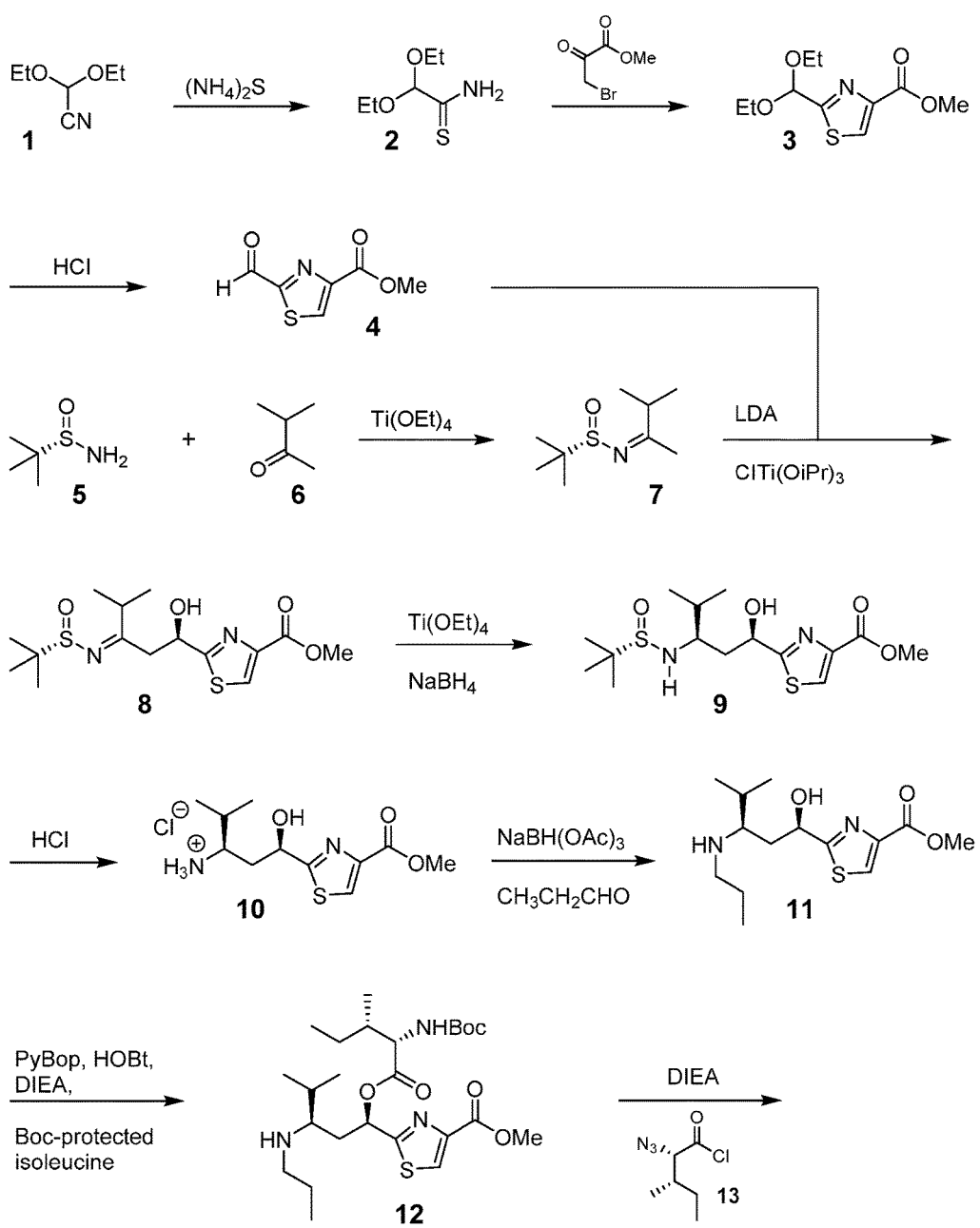
Figure 1B:
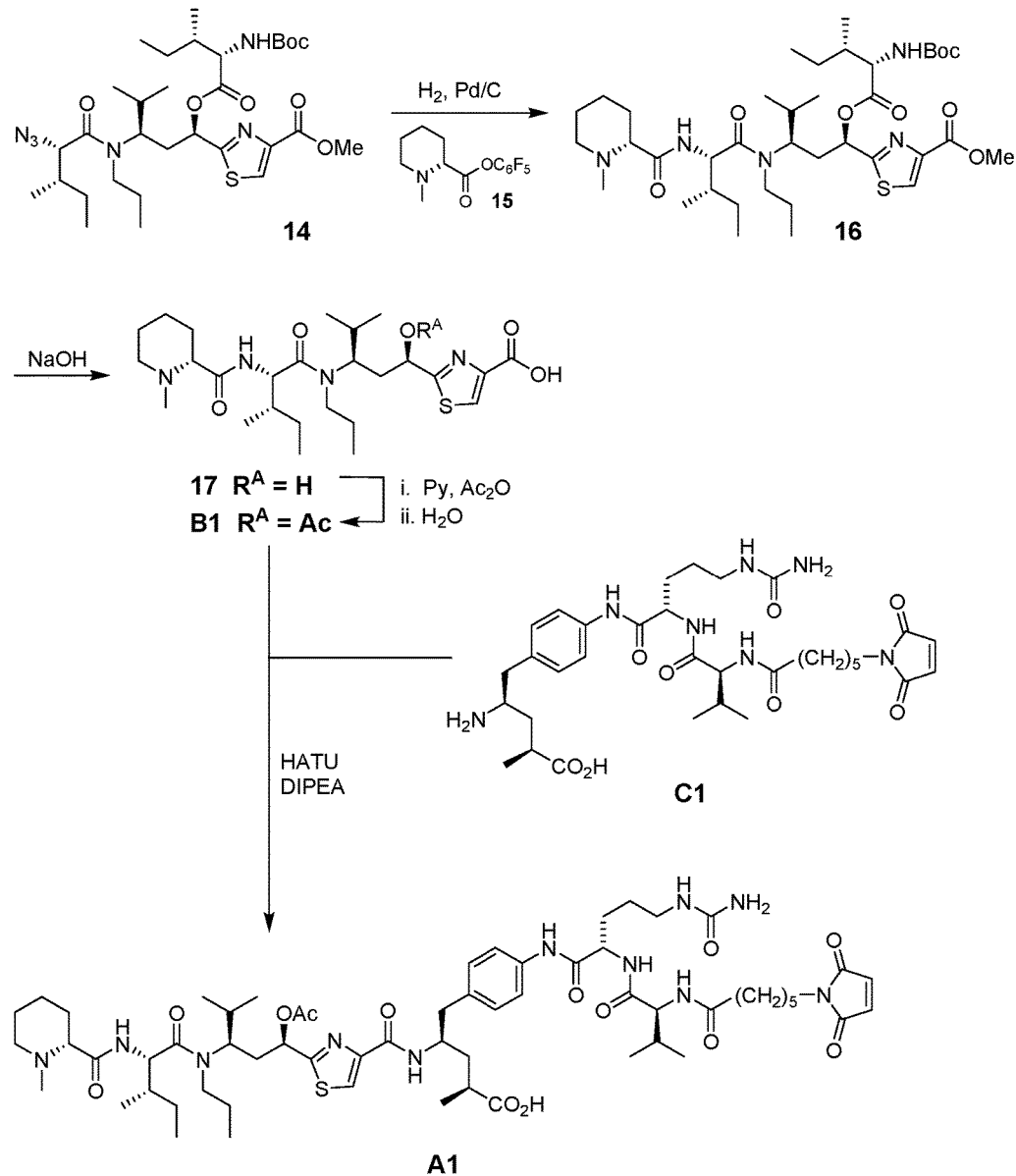
Figure 2:
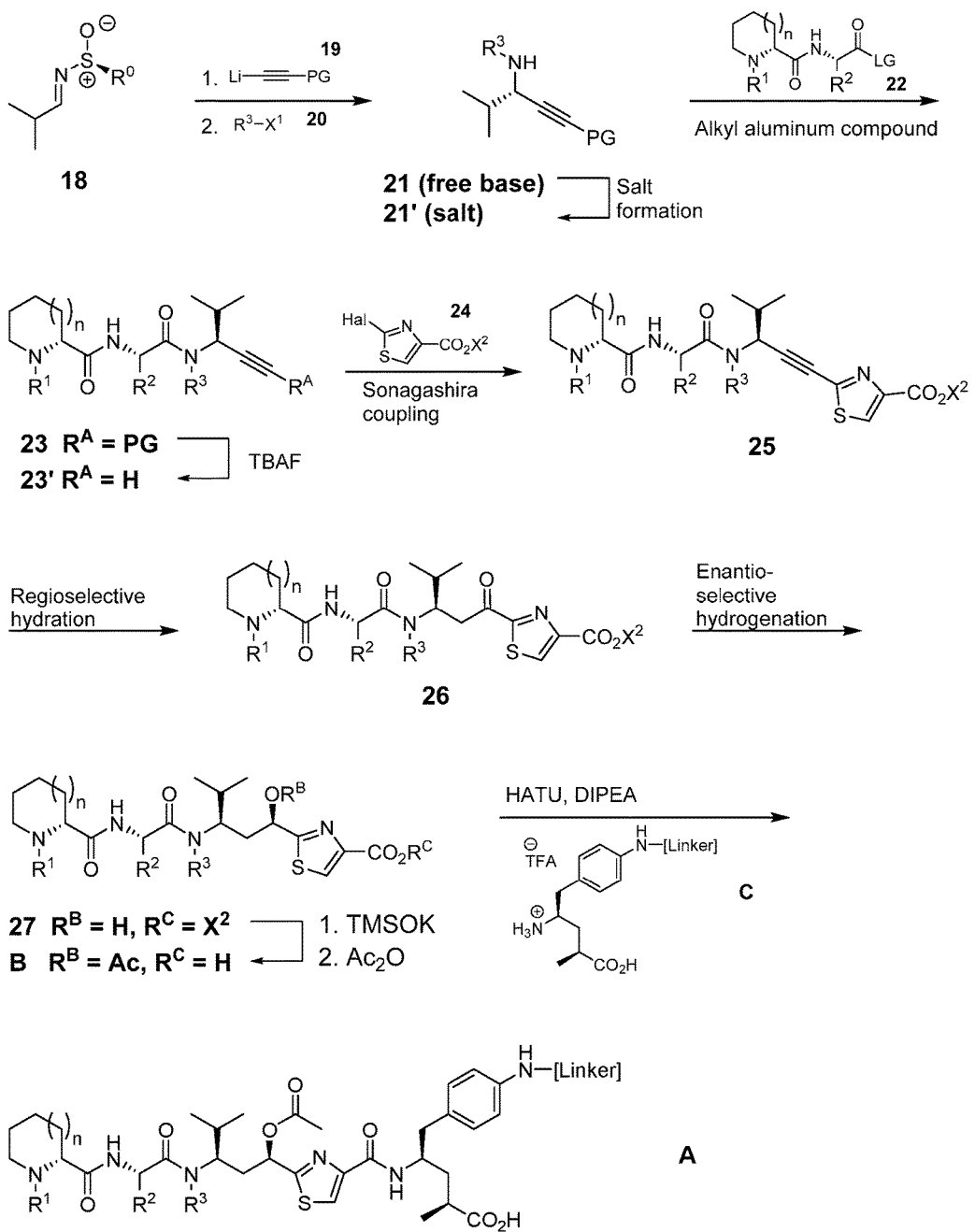
FIG. 2 shows a general scheme for the synthesis of analog/linkers A by the process of this invention.

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (C1q) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., Cellular and Molecular Immunology, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have crossreactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, nonaromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," it includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenyl-cyclohexylamine salt, benzathine salt, sodium salt, tetramethylammonium salt, and the like. Polymorphic crystalline forms and solvates are also encompassed within the scope of this invention.

In the formulae herein, a wavy line ( ~~~ ) transverse to a bond or an asterisk (*) at the end of the bond denotes a covalent attachment site. For instance, a statement that R is

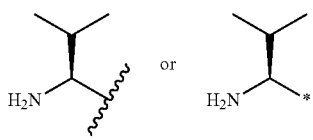

in the formula

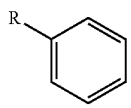

refers to

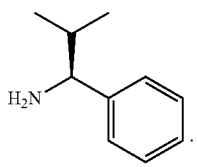

In the formulae of this specification, a bond traversing an aromatic ring between two carbons thereof means that the group attached to the bond may be located at any of the available positions of the aromatic ring. By way of illustration, the formula

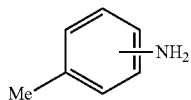

represents

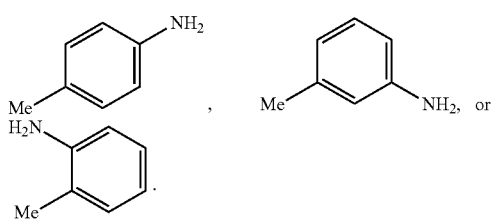

Where a reaction is described as being selective, as in "regioselective" or "enantioselective," or "diastereoselective," it means the reaction produces the desired isomer, enantiomer, diastereomer, or other product in a molar ratio of at least 51:49, more preferably at least 75:25, and most preferably at least 90:10 over the less desired isomer, enantiomer, diastereomer, or other product.

EMBODIMENTS

For ease of reference, the various aspects of the present invention are now discussed under appropriate sub-section headings. However, the teachings under each sub-section are not necessarily limited to the particular sub-section in which they occur.

Preferred Structural Variables

In compound 18, or another compound where this variable might occur, $R^0$ preferably is t-Bu.

In compounds 22, 23, 23', 25, 26, 27, B, and A, or another compound where this variable might occur, the subscript n preferably is 1.

In compounds 22, 23, 23', 25, 26, 27, B, and A, or another compound where this variable might occur, $R^1$ preferably is Me.

In compounds 22, 23, 23', 25, 26, 27, B, and A, or another compound where this variable might occur, $R^2$ preferably is (S) sec-butyl, that is,

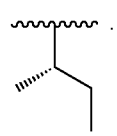

In compounds 20, 21, 23, 23', 25, 26, 27, B, and A, or another compound where this variable might occur, $R^3$ preferably is Me, Et, or n-Pr, most preferably n-Pr.

In compound 20, or another compound where this variable might occur, $X^1$ preferably is Br, with compound 20 preferably being MeBr, EtBr, or n-PrBr, and especially preferably n-PrBr.

In compounds 24, 25, 26, and 27, or another compound where this variable might occur, $X^2$ preferably is Me or Et, and more preferably Me.

Hal (halogen) in compound 24, or another compound where this variable might occur, preferably is Br.

In compounds 19, 21, 21', and 23, or another compound where this variable might occur, the silyl protective group PG preferably is trimethyl silyl (TMS), triethyl silyl (TES), triisopropyl silyl (TIPS), t-butyldiphenyl silyl (TBDPS), or t-butyldimethyl silyl (TBS or TBDMS), with triisopropyl silyl being especially preferred.

Leaving group LG in compound 22, or another compound where this variable might occur, preferably is

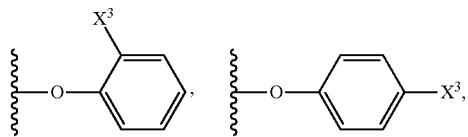

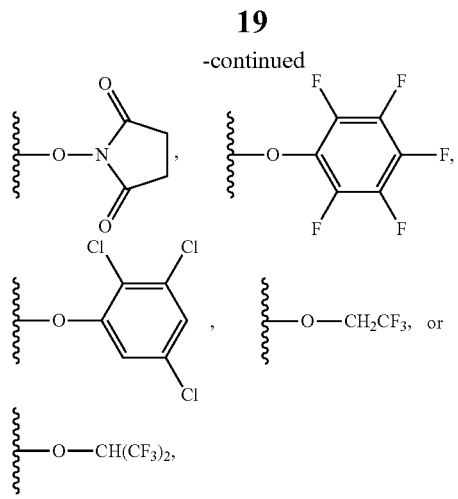

where X⁻³ is NO₂, F, Cl, Br, I, CF₃, or H. An especially preferred leaving group LG is

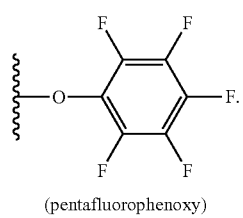 [SMILES: *Oc1c(F)c(F)c(F)c(F)c1F]

(pentafluorophenoxy)

First Aspect of the Invention

Referring to the preparation of compound 21 and its salts

21

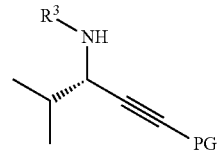

described in the first aspect of this invention, our method provides an efficient, single reaction vessel or "one pot" synthesis, involving the formation of C—C bond and C—N bonds. This method is advantageous compared to related procedures such as those in Wipf et al. 2010, which require separate work-up, isolation, and purification steps.

In compound 18, the group R⁰ preferably is t-Bu, corresponding to structure 18a

18a

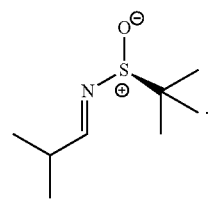

Without being bound by theory, it is believed that, when compounds 18 and 19 react, they form an intermediate INT-1 (using the preferred t-Bu group as an exemplar for R⁰):

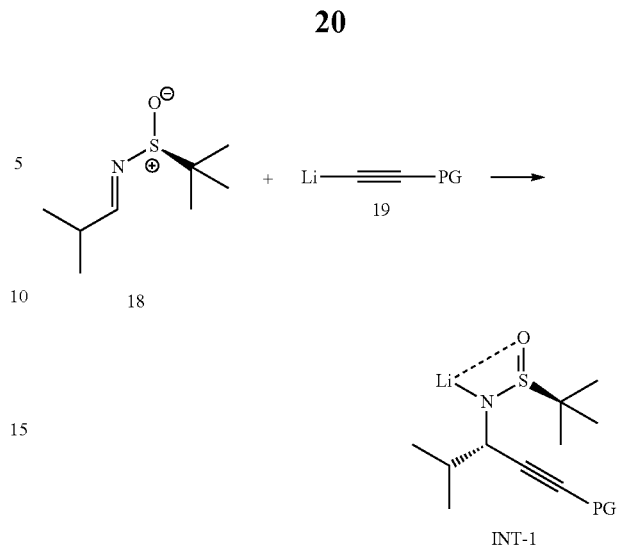

However, intermediate INT-1 is unreactive towards compound 20 (R³—X¹) because of intramolecular chelation between the lithium and the sulfinamide oxygen. Addition of a dechelating agent allows the reaction between intermediate INT-1 and compound 20 to proceed, resulting in intermediate INT-2. It is important that compound 20 be added to the reaction mixture before the addition of the de-chelating agent, so that the lithium is rendered reactive in the presence of compound 20.

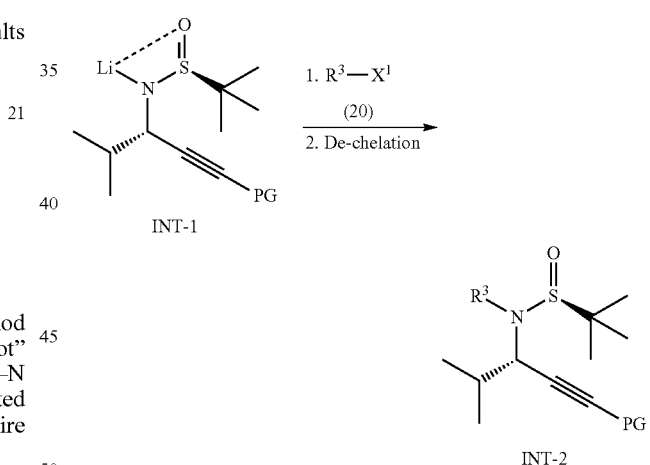

The de-chelating agent preferably is selected from the group consisting of N,N-dimethylformamide (DMF), dimethylsulfoxide (DMSO), hexamethylphosphoramide (HMPA), 1,3-dimethyl-3,4,5,6-tetrahydro-2(1H)pyrimidinone (DMPU), and N,N-dimethylacetamide (DMAC), with DMF being especially preferred.

Preferably, compound 21 is isolated and stored as its salt (especially a hydrochloride salt). The salt can be used as such in the next step, being converted in situ to the free base.

Addition of the primary or secondary alcohol and the anion source to intermediate INT-2 leads to removal of the sulfinamide group as a sulfinate ester (using ethanol as an exemplar for the alcohol), followed by in situ formation of salt 21':

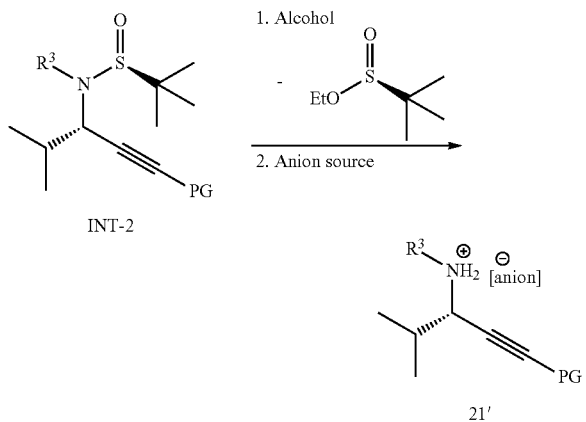

INT-2

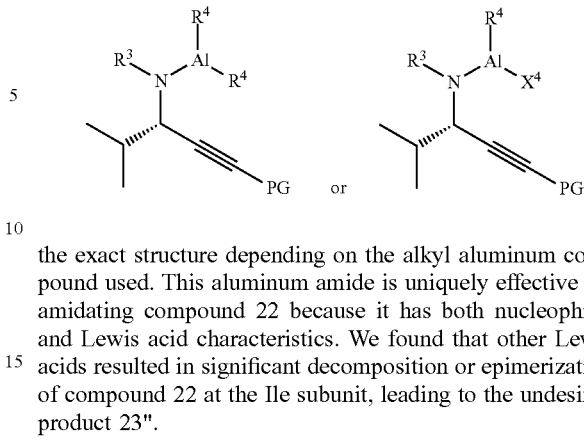

21'

The primary or secondary alcohol preferably is a $C_1$-$C_4$ alcohol such as methanol, ethanol, n-propanol, isopropanol, n-butanol, or 2-butanol; more preferably ethanol.

The anion source preferably is trimethylchlorosilane (TMSCl), thionyl chloride, or acetyl chloride (more preferably TMSCl), which provide chloride as the anion.

In a preferred embodiment of this first aspect, $R^3$ is n-Pr, $X^1$ is Br, the de-chelating agent is DMF, and PG is triisopropyl silyl.

Second Aspect of the Invention

Referring to the preparation of compound 23

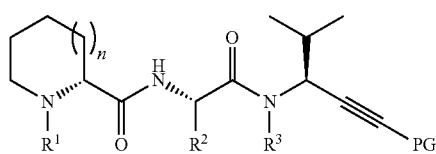

described in the second aspect of this invention, we found that conventional coupling conditions do not work with compound 21 to amidate it with compound 22 with the desired stereochemistry. Among the conventional amidation reagents we unsuccessfully tried were N(3-dimethylaminopropyl)-N'-ethylcarbodiimide (EDAC)/hydroxybenzotriazole (HOBt), N,N,N',N'-tetramethyl-O-(7-azabenzotriazol-1-yl)uronium hexafluorophosphate (HATU), bromotripyrrolidinophosphonium hexafluorophosphate (PyBrop), acid chlorides, and acid fluorides. In experiments in which the $R^3$ group was varied between Me, Et, and n-Pr, only the smallest alkyl group (Me) gave any product, indicating a strong steric effect due to the size of $R^3$.

We found that use of a haloalkyl aluminum compound unexpectedly is successful where the conventional reagents were not. Suitable haloalkyl aluminum compounds are of the formula $Al(X^4)_2R^4$ or $Al(R^4)_2X^4$, where $R^4$ is methyl, ethyl, or isobutyl and $X^4$ is Cl or Br. Preferably, the haloalkyl aluminum compound is $Al(R^4)_2X^4$; more preferably, it is diethyl aluminum chloride ($Et_2AlCl$). For a disclosure on the use of the related trialkyl aluminum compound $Al(Me)_3$ for the amidation of simple substrates, see Li et al. 2012.

Without being bound by theory, it is believed that the amidation reaction proceeds via an intermediate aluminum amide such as

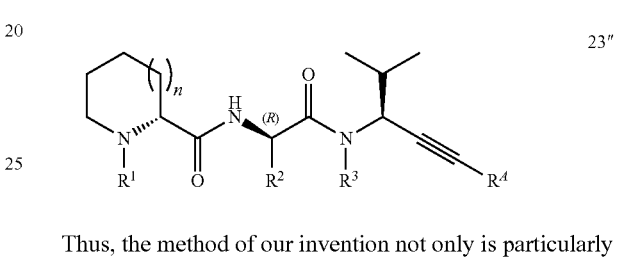

the exact structure depending on the alkyl aluminum compound used. This aluminum amide is uniquely effective for amidating compound 22 because it has both nucleophilic and Lewis acid characteristics. We found that other Lewis acids resulted in significant decomposition or epimerization of compound 22 at the Ile subunit, leading to the undesired product 23".

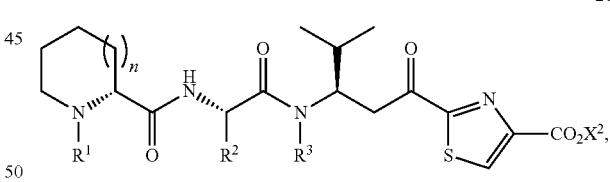

Thus, the method of our invention not only is particularly suitable where the group $R^3$ is larger in size (as in n-Pr) and is preferably applied to such groups, but also is beneficial in avoiding or reducing epimerization.

In a preferred embodiment of this second aspect, the haloalkyl aluminum compound is $Al(X^4)_2R^4$ or $Al(R^4)_2X^4$, where $R^4$ is methyl, ethyl, or isobutyl, and $X^4$ is Cl or Br and more preferably is $Et_2AlCl$. The structural variables preferably are as follows: n is 1; $R^1$ is Me; $R^2$ is (S) sec-butyl; $R^3$ is n-Pr; PG is triisopropyl silyl; and LG is pentafluorophenoxy.

Third Aspect of the Invention

The preparation of compound 26

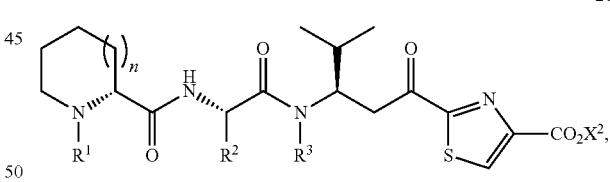

described in the third aspect of the invention, is noteworthy for its regioselectivity, with metalation by a silicon or boron metalating agent taking place exclusively at the carbon adjacent to the thiazole ring.

Exemplary suitable metalating agents are $(RO)_2SiH$, $R_3SiH$, $R_2BH$, $(RO)RBH$, and $(RO)_2BH$, each of which has an Si—H or B—H moiety, where each R is independently $C_1$-$C_4$ alkyl or benzyl. Metalating agents having an Si—H bond are preferred. We had most success with $(EtO)_2MeSiH$, but also some success with $BnMe_2SiH$. In addition, the method of this invention can be extended to hydroboration (Lipshutz et al. 2008) and hydroamination (Shi et al. 2015).

Without being bound by theory, it is believed that an intermediate metalated product INT-3 is formed, having the structure shown below (using $(EtO)_2MeSiH$ as an exemplar), which can then be oxidized to afford compound 26.

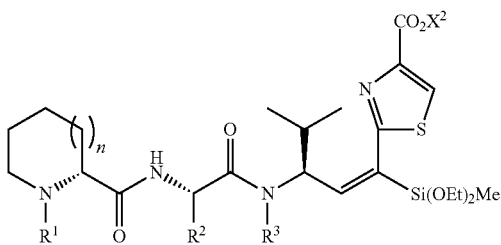

INT-3

Figure 3A:
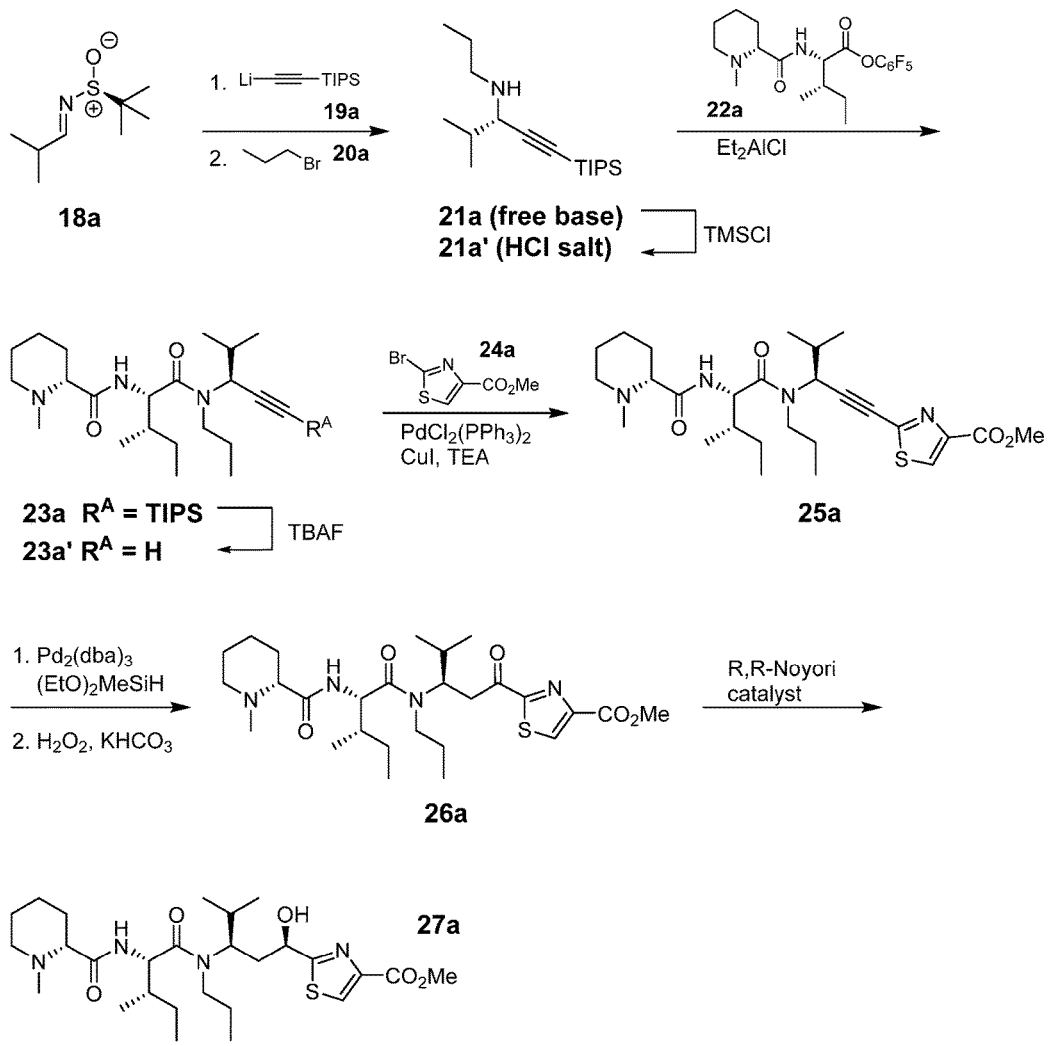
FIGS. 3A and 3B show, in combination, the synthesis of a specific tubulysin analog/linker compound by the process of this invention.

The regioselectivity of the metalation reaction was confirmed by NMR data on specific intermediate INT-3a, corresponding to the metalation of compound 26a (FIG. 3A).

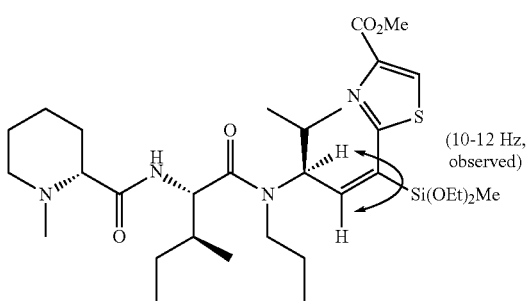

INT-3a
(10-12 Hz, observed)

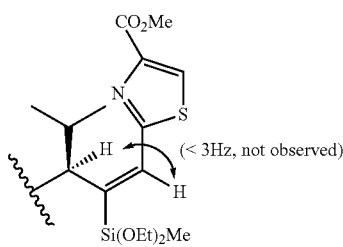

(< 3Hz, not observed)

A scalar coupling of about 10-12 Hz was observed between the two hydrogens pointed to by the two-headed arrow, consistent with the desired regiochemistry. Had the metalation taken place with the opposite regiochemistry, the expected coupling would have been less than 3 Hz—but such coupling was not observed.

Without being bound by theory, we hypothesize that the regioselectivity can be explained as follows: the alkyne, being conjugated to an electron-deficient heterocycle, is polarized such that the alkyne carbon distal to the heterocycle is more electron deficient than the alkyne carbon proximal to the heterocycle. The migratory insertion of a palladium(+2) hydride would be expected to place the electronegative hydride ligand at the distal carbon and the electropositive palladium(+2) at the proximal carbon. After this event, reductive elimination of the silicon ligand onto the newly-formed vinyl ligand leads to the vinylsilane. Our results are consistent with other reports on the regioselelctive metalation or other addition reactions to polarized alkynes. See, for example, Lishutz et al. 2008; Rooke et al. 2010, 2012, and 2014; Shi et al. 2015; and Sumida et al. 2012.

A preferred metal catalyst for the addition reaction is $Pd_2(dba)_3$, but other catalysts, especially complexes of Pt and Pd, can be used, such as $Pt(dba)_2$, $PtO_2$, $PtCl_2$, $[(Cy_3P)(Me_2BzSi)(\mu-H)Pt]2$, and $[Pd(dtbpf)Cl_2]$; as disclosed in Lishutz et al. 2008; Rooke et al. 2010, 2012, and 2014; Shi et al. 2015; and Sumida et al. 2012; the disclosures of which are incorporated herein by reference. Other transition metal catalysts can also be used, such as $RhCl(PPh_3)_3$ (Wilkinson's catalyst) and $[RuCl_2(C_6H_6)]_2$. However, some catalysts may not provide the desired regioselectivity, so some experimentation may be needed.

A variety of oxidizing agents can be used to oxidize intermediate INT-3. Examples include $H_2O_2$ (hydrogen peroxide), peroxy acids, urea hydrogen peroxide complex and $K_2O_2$. Generally, peroxide agents are preferred, especially $H_2O_2$ (hydrogen peroxide) and peroxy acids. In principle, reagents with an M-O—O— fragment, where M is H, Li, Na, or K are potentially suitable. The oxidizing agent can be generated in situ, such as peroxyacetic acid from acetic anhydride and $H_2O_2$. These so-called Tamao-Fleming oxidations typically employ fluoride anion, most often supplied as potassium fluoride or tetrabutylammonium fluoride. Typically solvents include methanol, tetrahydofuran, DMF, and water.

In an especially preferred combination, the metal catalyst is tris(dibenzylideneacetone)dipalladium(0) ($Pd_2(dba)_3$), the metalating agent is $(EtO)_2SiMeH$ and the oxidizing agent is hydrogen peroxide in a potassium carbonate/methanol medium.

In a preferred embodiment of this third aspect, the metal catalyst is tris(dibenzylideneacetone)dipalladium(0), the metalating agent is $(EtO)_2SiMeH$, and the oxidizing agent is hydrogen peroxide. The structural variables preferably are as follows: n is 1, $R^1$ is Me, $R^2$ is (S) sec-butyl, $R^3$ is n-Pr, and $X^2$ is $C_1$-$C_3$ alkyl.

Fourth Aspect of the Invention

We now refer to the preparation of compound 27 by the enantioselective hydrogenation of the ketone group of compound 26, described in the fourth aspect of the invention, using an asymmetric hydrogenation catalyst.

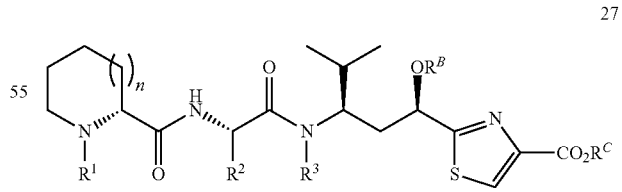

27

Preferably, the asymmetric hydrogenation catalyst is a Noyori catalyst, as affording superior enantioselectivity. If an R,R-Noyori catalyst is used, desired compound 27 is obtained with greater than 99:1 diastereoselectivity. Conversely, if an S,S-Noyori catalyst is used, compound 27' with the reversed stereochemistry at the relevant position is selectively obtained.

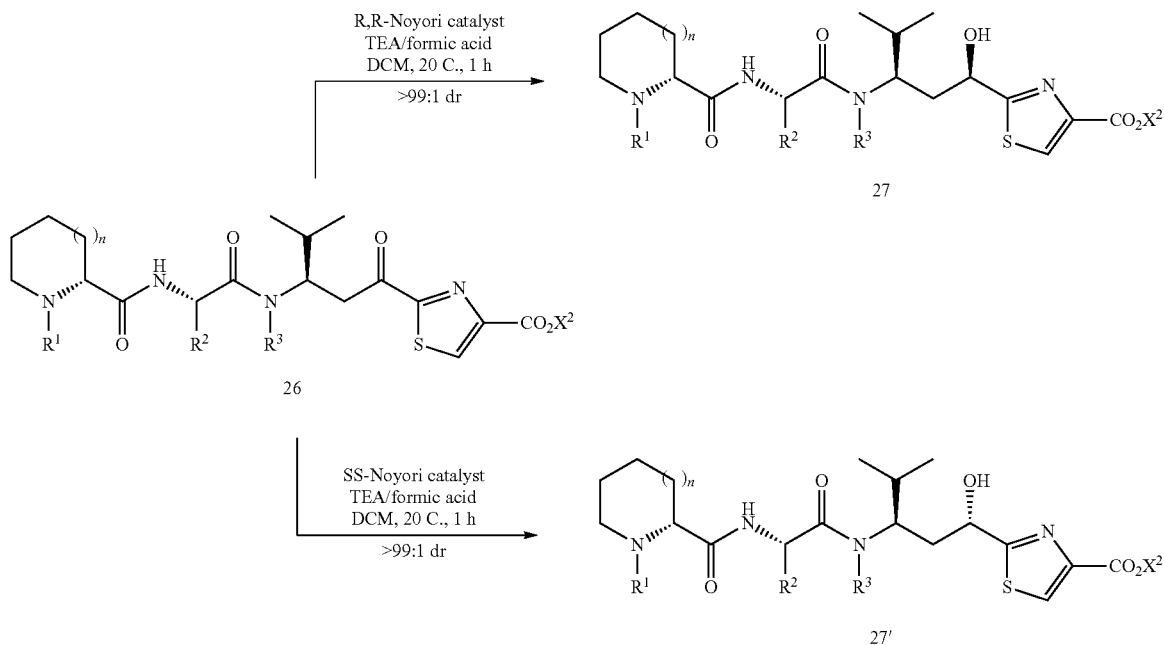

A different asymmetric reducing agent such as (S)-CBS (Richter 2015; Zanda et al. 2013) is not as desirable with compound 26 because the $BH_3$ used in that method could react with compound 26 at both the acidic amide proton and basic nitrogen of the Mep subunit. Further, the Noyori reduction process advantageously can be performed at ambient temperature and generates fewer volatile by-products.

A preferred RR-Noyori catalyst is the commercially available coordination compound [N-[(1R,2R)-2-(amino-κN)-1,2-diphenylethyl]-4-methylbenzenesulfonamidato-κN] chloro[(1,2,3,4,5,6-η)-1,3,5-trimethylbenzene]-ruthenium (also known as RuCl[(R,R)TsDPEN](mesitylene); CAS Registry Number 174813-82-2), whose structure is shown below.

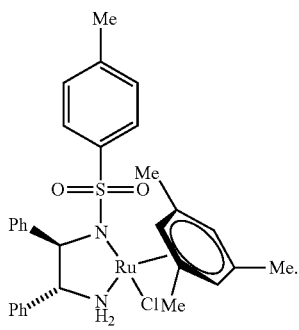

This catalyst provides "ligand controlled" stereochemistry in the reduction, which is preferred, compared to a catalyst that provides "substrate controlled" stereochemistry, as the latter instance either leads to the undesired diastereomer or a low diastereomeric ratio. Those skilled in the art will understand that other Noyori catalysts are known in the art and can be used.

Preferably, the reduction is conducted using a "transfer hydrogenation" technique, in which formic acid and trim-ethylamine are combined as an easy and convenient in situ source of "hydrogen" reductant. This technique is preferable to using a pressurized vessel charged with hydrogen gas, considering the specialized equipment and hazards entailed by the latter technique.

In a preferred embodiment of this fourth aspect, the asymmetric hydrogenation catalyst is an R,R-Noyori catalyst, preferably

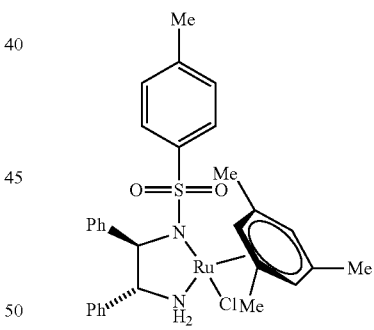

in combination with these structural variables: n is 1, $R^1$ is Me, $R^2$ is (S) sec-butyl, $R^3$ is n-Pr, and $X^2$ is $C_1$-$C_3$ alkyl.

EXAMPLES

The practice of this invention can be further understood by reference to the following examples, which are provided by way of illustration and not of limitation.

Example 1—Compound 21a

This example relates to the preparation of compound 21a and its hydrochloride salt 21a' (FIG. 3A).

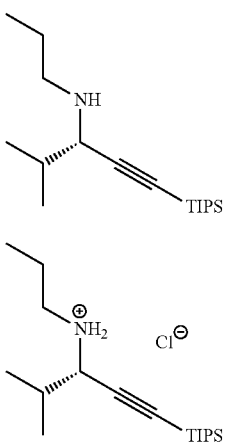

(Triisopropylsilyl)acetylene 19a (96.8 mL, 1.50 equiv.), toluene (500 mL), and tetrahydrofuran (THF, 70.1 mL, 3.00 equiv.) were added to a 2 L CHEMGLASS™ reactor. The mixture was cooled to −15° C. N-Butyllithium (2 mol/L) in cyclohexane (215 mL, 1.50 equiv.) was added slowly, maintaining the reaction temperature between −10 and 0° C. After addition, the reaction mixture was held for 5 min at 0° C. A toluene solution of imine 18a (100 g, 50 g net weight of 18a, 1.00 equiv.) was added at −5 to about 0° C. After addition, the mixture was held at 0° C. for 0.5 h. In-process analysis showed full consumption of imine 18a. 1-Bromopropane (104 mL, 4.0 equiv.) was added, followed by DMF (178 mL, 8.0 equiv.). The reaction mixture was stirred at room temperature (RT) for 16 h. In-process analysis showed complete conversion of the sulfonamide intermediate. The reaction was quenched with 500 mL 15 wt % aqueous $NH_4OAc$ and stirred for 10 min. The aqueous and organic phases were split and washed with 500 mL water, followed by 500 mL of aqueous 10% NaCl. The organic layer was dried over $Na_2SO_4$ and concentrated to an oil. Methyl t-butyl ether (MTBE, 1000 mL) was added to the oil, followed by ethanol (33.4 mL, 2.0 equiv.) and then TMSCl (73 mL, 2.0 equiv.). A heavy slurry formed immediately and was aged for 1 h; cooled to 0° C.; and aged further for 2 h. The crystals formed were filtered and washed with 2×300 mL MTBE. The wet cake was dried under vacuum at 60° C. until constant weight, to provide 82 g of salt 21a', yield 86%; chiral purity: S/R=99.5/0.5. HRMS M/Z Expected: 295.27; Found: (M+H) 296.2768.

Example 2—Compound 22a

Figure 4:
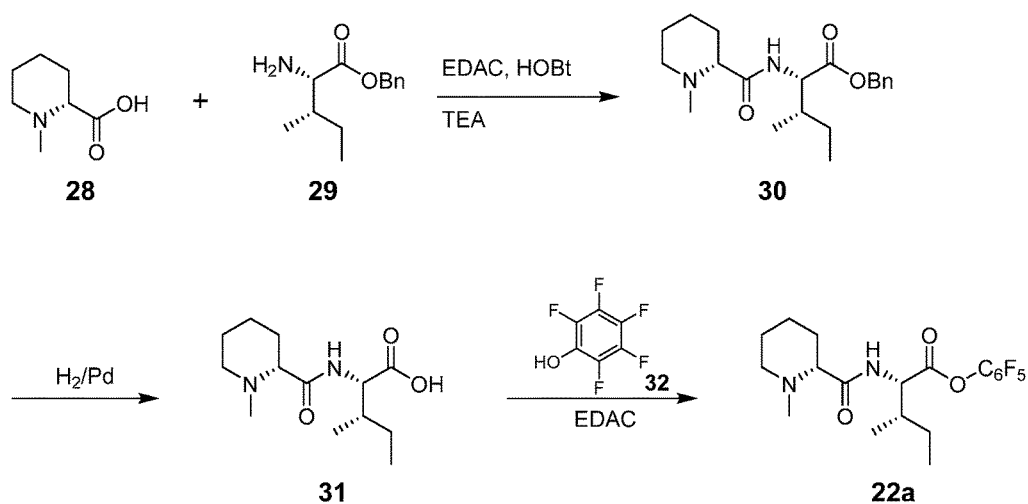
FIG. 4 shows a scheme for the synthesis of an intermediate used in this invention.

This example relates to the preparation of compound 22a (FIG. 4).

The following materials were added to a 1 L CHEMGLASS™ reactor: acid 28 (100 g, 1.0 equiv.), isoleucine benzyl ester 29 (43.7 g, 1.2 equiv.), dichloromethane (DCM, 500 mL), $ET_3N$ (44.3 mL, 1.25 equiv.), 1-hydroxybenzotriazole (HOBt, 43.0 g, 1.25 equiv.), and 1-(3-dimethylaminopropyl)-3-ethylcarbodiimide hydrochloride (EDAC, 61 g, 1.25 equiv.). The resulting mixture was stirred at RT for 16 h. In-process analysis showed full conversion of ester 29. 400 mL water was added to the reaction mixture. The aqueous layer was separated as waste and the organic layer was washed with 400 mL saturated $Na_2CO_3$, followed by 200 mL aqueous 10% NaCl and drying over $Na_2SO_4$. The solvent was removed under vacuum to leave a heavy oil that was dissolved in 500 mL MTBE. DARCO™ G-60 activated charcoal (10 g, 10 wt/wt % vs. starting material) was added. The mixture was stirred for 1 h. The activated charcoal was filtered off and rinsed with 100 mL MTBE. The solvent was removed under vacuum to leave a thick oil. This oil was dissolved in EtOH (500 mL) for hydrogenolysis: 10 g catalyst (10% Pd/C, 50% wet), 40 psi $H_2$, 16 h until full consumption of benzyl ester 30. The mixture was filtered to remove the Pd catalyst and concentrated to about 100 mL. MTBE (500 mL) was added slowly and crystals formed. The slurry was aged at RT overnight. The crystals were filtered and washed with 100 mL MTBE. The wet cake was dried under vacuum at 50° C. to yield dipeptide 31 (52.5 g) as sandy crystals, yield 85%. HRMS M/Z Expected: 256.18; Found: (M+H) 257.1860.

To a solution of dipeptide 31 (1.0 equiv; 180 g, 639 mmol, 91 wt %) in DCM (0.9 L, 5 mL/g) was add pentafluorophenol 32 (1.11 equiv; 133 g, 708 mmol, 98 wt %), followed by EDAC (1.15 equiv; 141 g, 735 mmol) at 21° C. The reaction progress was monitored by HPLC. After 4 h, heptane (1.5 L, 8 mL/g) was added to the reaction mixture, followed by water (1.0 L, 5.6 mL/g). The mixture was agitated for 10 min, and the aqueous phase was removed. The organic phase was washed with aqueous $Na_2CO_3$ (10 wt %; 1.0 L×2), followed by aqueous $KH_2PO_4$ (5 wt %; 1.0 L). The resulting organic phase was dried with $MgSO_4$ (0.3 kg). After the removal of the drying agent by filtration, the liquid phase was concentrated in vacuo from 3.0 L to 1.8 L at <35° C., during process which a slurry formed. The resulting slurry was cooled to 0° C. over 1.5 h and stirred for 13 h at that temperature. The batch was filtered, and rinsed with cold heptane (0° C.; 0.2 L). The rinse was applied to the filter cake. The filtrate was concentrated in vacuo to about 0.35 L at <35° C., and the resulting slurry was cooled to 0° C. and held for 1 h before filtration. The resulting filter cake was washed with cold heptane (0.1 L). The filter cakes were combined and dried in vacuo at 21° C., providing compound 22a as a white solid (237 g, 98.4 wt %; 87% yield). HRMS M/Z Expected: 422.16; Found: (M+H) 423.1702.

Example 3—Compound 23a

This example relates to the preparation of compound 23a (FIG. 3A).

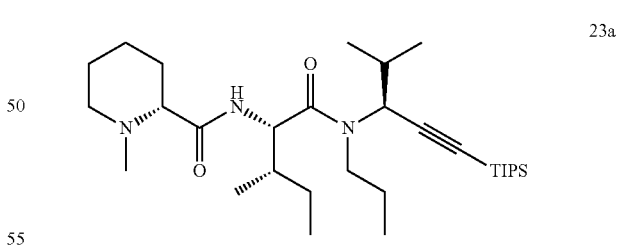

Hydrochloride 21a' (2.0 equiv; 381 g, 1.15 mol, 100 wt %) was added into a mixture of toluene (1.25 L, 5 mL/g) and aqueous $Na_2CO_3$ (10 wt %, 1.5 L, 6 mL/g) at 21° C. The resulting slurry was stirred until all the solids were dissolved. The aqueous phase was removed and $MgSO_4$ (0.3 kg) was added to the organic layer. After 20 min, the $MgSO_4$ was filtered, and the process line was rinsed with toluene (150 mL, 0.6 mL/g). The rinse was applied to the filter cake wash. The combined filtrates were transferred into a 5-liter reactor. Toluene (100 mL, 0.4 mL/g) was used to rinse and complete the transfer. Diethylaluminum chloride (1 mol/L)

in hexanes (0.5 equiv; 0.29 L, 290 mmol, 1 mol/L) was then added at 20° C., resulting in a mild exotherm and increase in temperature to 25° C. The mixture was stirred at 20-25° C. for 30 min. Compound 22a (1.0 equiv; 250 g, 580 mmol, 98 wt %) was then added. The reaction mixture was stirred under $N_2$ at 21° C. HPLC was used to monitor the reaction progress. After 5 days, the reaction mixture was added to a mixture of MTBE (1.0 L, 4 mL/g) and aqueous citric acid (15 wt %, 1.67 kg, 6.5 g/g) with a rinse of MTBE (1.5 L, 6 mL/g) to complete the transfer. The resulting mixture was stirred for 20 min. The aqueous phase was removed and the organic layer was washed with aqueous NaOH (2 N, 1.3 L×2; 5 mL/g×2). Aqueous $NaHCO_3$ (150 g in 2 L of water) was then added to the organic phase, followed by acetyl chloride (2.5 equiv.; 104 mL, 1.46 mol). After stirring for 0.5 h, the aqueous phase was removed and the organic phase was dried over $MgSO_4$ (0.22 kg). The $MgSO_4$ was removed by filtration and the process line was rinsed with heptane (0.2 L). The stream was transferred into a 10 L reactor, with a rinse of heptane (0.2 L) to complete the transfer. MeOH (2.6 equiv; 62 mL, 1.53 mmol) was added, followed by chlorotrimethylsilane (1.5 equiv; 111 mL, 873 mmol). After the addition, a white precipitate formed and the resulting slurry was stirred for 12 h before cooling to 0° C. After 5 h at 0° C., the slurry was filtered, and 2 L of the filtrate was used to rinse the reactor, and the rinse was applied to the filter cake. The cake was then washed with mixed heptane/MTBE (1:1; 0.35 L×2), providing compound 23a HCl salt as a white solid (229.5 g; 97.0 wt %; 67% yield). HRMS M/Z Expected: 533.44; Found: (M+H) 534.4449.

Example 4—Compound 23a'

This example relates to the preparation of compound 23a' (FIG. 3A).

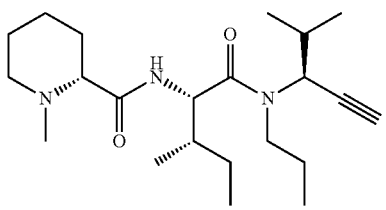

23a'

Compound 23a HCl salt (1.0 equiv; 227 g, 386 mmol, 97 mass %) was mixed with MTBE (0.91 L, 4 mL/g) and aqueous $Na_2CO_3$ (15 wt %, 0.79 L, 3.5 mL/g). After the solids were dissolved, the aqueous phase was removed, and the organic layer was dried over $MgSO_4$ (50 g). The $MgSO_4$ was removed by filtration and the filtrate was transferred to a 5 L reactor with a rinse of MTBE (0.23 L 1 mL/g) to complete the transfer. THF (0.23 L, 1 mL/g) was added to the filtrate, followed by a solution of tetrabutylammonium fluoride (TBAF, 1 mol/L) in THF (1.24 equiv.; 0.48 L, 0.480 mmol, 1 mol/L) at 21° C. After 1 h, HPLC analysis showed the reaction was complete. MTBE (1.1 L, 5 mL/g) and hexane (1.1 L, 5 mL/g) were added to the reaction mixture, followed by aqueous $Na_2CO_3$ (10 wt %, 1.1 L, 5 mL/g). The aqueous phase was removed and the organic layer was washed with aqueous $Na_2CO_3$ (5 wt %, 1.1 L×2), and dried over $MgSO_4$ (100 g). After filtration to remove the $MgSO_4$, the filtrate was concentrated in vacuo to provide compound 23a' as a colorless oil (225 g, 64.6 wt %; 99% yield). HRMS M/Z Expected: 377.30; Found: (M+H) 378.3115.

Example 5—Compound 25a

This example relates to the preparation of compound 25a (FIG. 3A).

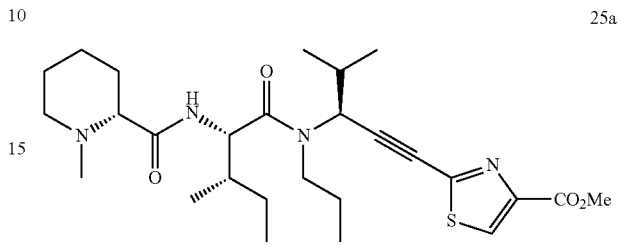

25a

To a 1 L round-bottom flask was added compound 23a' (40 g, 66.743 mmol, 63 mass %), thiazole 24a (CAS Reg. No. 170235-26-4, 1.3 equiv., 86.765 mmol, 97.000 mass %), and DMF (5 mL/g, 3810 mmol). To the resulting thin slurry was added triethylamine (TEA, 5 equiv., 333.71 mmol) and bis(triphenylphosphine)palladium(II) dichloride (0.02 equiv., 1.3349 mmol). Cuprous iodide (0.02 equiv., 1.3349 mmol) was then added. The reaction was heated to 55-60° C. for 12 h. The reaction was monitored by HPLC analysis. The reaction mixture was cooled to 20° C. and diluted with MTBE (10 vol). To this mixture was added a solution of 2% aqueous N-acetyl cysteine (15 vol). The biphasic mixture was stirred for 30 min at RT. The layers were separated and the organic layer was washed with 5% aq. $NaHCO_3$, and then directly treated with 50 wt % DARCO™ G60 activated charcoal and stirred for 30 min at RT. The charcoal was removed by filtration through a pad of CELITE™ diatomaceous earth. The water was removed by azeotropic distillation. Compound 25a was isolated as its HCl salt (25 g, 75% yield) after addition of anhydrous HCl (2 equiv., 3 M in cyclopentyl methyl ether (CPME)). HRMS M/Z Expected: 518.29; Found: (M+H) 519.3000.

Example 6—Compound 26a'

This example relates to the synthesis of compound 26a (FIG. 3A) by the regioselective hydrosilylation of compound 25a followed by a Tamao-Fleming oxidation.

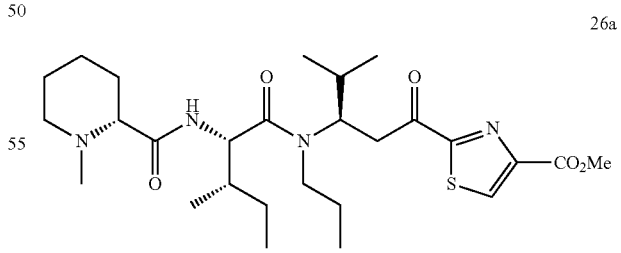

26a

Compound 25a (9.0643 g, 16.6 mmol, 95.0 mass %) was added to a 500 mL round-bottom flask equipped with a magnetic stir bar. Toluene (36.6 mL, 240 mmol, 99.8) was added. The reaction vessel was sealed with a rubber septum and sparged with $N_2$ for 5 min. The reaction vessel was opened and tricyclohexylphosphonium tetrafluoroborate (0.120 equiv., 1.99 mmol, 98.0 mass %) was added. The reaction vessel was sealed and sparged as before. The reaction mixture was stirred vigorously at RT for approximately 1 h. The reaction vessel was reopened and tris (dibenzylideneacetone)dipalladium(0) (Pd$_2$(dba)$_3$, 0.481 g, 0499 mmol, 95.0 mass %) was added. The reaction vessel was sealed and sparged as before. Diethoxymethylsilane (8.30 mL, 49.8 mmol, 96.0 mass %) was added via syringe under N$_2$. Stirring was continued at RT under N$_2$. After 24 h, HPLC analysis showed complete consumption of the reactants. The reaction mixture was poured onto a pad of silica gel (about 5 cm thick) and eluted with about 250 mL 1:1 acetone:hexanes. The solution obtained was concentrated to dryness under vacuum.

To a 250 mL jacketed reactor equipped with an overhead stirrer was added MeOH (45 mL, 99.5 mass %) followed by KF (0.990 g, 16.9 mmol, 99.0 mass %). Overhead stirring was initiated at about 260 RPM. Once the KF had dissolved, cooling was applied using an external chiller set to −20° C., aiming for a reaction mixture temperature below −10° C. K$_2$CO$_3$ (3.34 g, 33.2 mmol, 99.5 mass %) was added, using MeOH (45 mL, 99.5 mass %) to rinse the funnel used for addition of the solids. The stirring rate was increased to ~330 RPM. Aqueous H$_2$O$_2$ (3.2 mL, 33 mmol, 35 mass %) was added via syringe under ambient atmosphere. Separately, MeOH (~22.5 mL, 99.5 mass %) was added to the vinylsilane intermediate. Then Et$_3$N (18.5 mL, 131 mmol, 99.0 mass %) was added. The mixture was swirled by hand to aid dissolution. This mixture was transferred to a 250 mL addition funnel. The original flask was rinsed with MeOH (~22.5 mL, 99.5 mass %) and the rinses were also transferred to the addition funnel. The addition funnel was affixed to the top of the reactor and dropwise addition was initiated. The total addition time was 22 min, using MeOH (~9 mL, 99.5 mass %) to rinse the addition funnel walls. The reaction mixture was stirred with cooling. At 50 min after completion of addition, the reaction mixture was analyzed by HPLC and judged to be complete (silane completely consumed). Approximately 2 h after the end of addition, a solution of Na$_2$SO$_3$ (3.51 g 33.4 mmol, 99 mass %) in water (~15 mL) was added dropwise over several minutes to quench the remaining peroxide. The internal temperature rose from −14° C. to −6.0° C. during the process. After the addition of the Na$_2$SO$_3$ solution, the external chiller was set to 21.5° C. and the reaction mixture was allowed to warm to about 19° C. Then the reaction mixture was drained from the reactor, which was rinsed with water (~15 mL) and then isopropyl acetate (~45 mL). The resulting greenish-grey suspension was filtered over a wet-packed (isopropyl acetate) bed of CELITE™ using vacuum. A dark brown, homogenous filtrate was obtained. The filtrate was poured into a separatory funnel and to this was added saturated aqueous sodium bicarbonate (~90 mL). The resulting layers were separated. The aqueous portion was extracted twice successively using fresh isopropyl acetate (~45 mL) each time. The combined organic portions were then washed with fresh saturated aqueous NaHCO$_3$ (~90 mL), dried over Na$_2$SO$_4$, filtered, and evaporated to dryness under vacuum. The crude residue was then taken up in a few milliliters of toluene and evaporated to dryness. To the neat residue was added MTBE (~90 mL) and isopropanol (2.58 mL, 33.5 mmol, 99.5 mass %). Chlorotrimethylsilane (4.30 mL, 33.2 mmol, 98.0 mass %) was then added dropwise via syringe under moderate magnetic stirring. The heterogeneous mixture was stirred overnight. The next day it was filtered using a tared, disposable plastic fritted funnel. The flask was rinsed with fresh MTBE (~18 mL) and the rinses were poured onto the wet cake, rinsing again with fresh MTBE (~27 mL). The funnel with solid was then dried in a vacuum (50° C.) for several hours. There was obtained compound 26a as a tan powder (6.2610 g, 65.8% isolated yield, uncorrected for purity). HRMS M/Z Expected: 536.30; Found: (M+H) 537.3105.

Example 7—Compound 27a

This example relates to the synthesis of compound 27a (FIG. 3A).

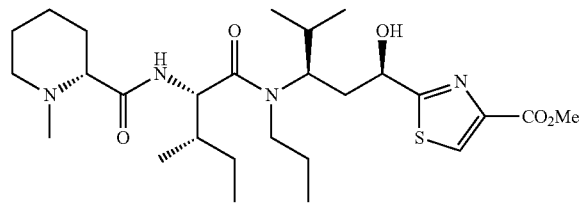

27a

Compound 26a (5.4 g, 1 equiv.) and DCM (15 vol, 80 mL) were added to a 500 mL 3-neck round-bottom flask. To this reaction mixture was added Et$_3$N (4.8 mL, 4 equiv.), followed by the dropwise addition of formic acid (2.6 mL, 8 equiv., exothermic). The resulting mixture was stirred for 30 min at RT. The Noyori catalyst RuCl[(R,R)-TsDPEN](mesitylene) (1.5 mol %, 85 mg) was added and the reaction was stirred at RT overnight (no less than 12 h). Reaction completion was determined by HPLC analysis (>99.5% conversion). The reaction mixture was quenched by the addition of aqueous NH$_4$OAc (10 vol, 50 mL) and the resulting biphasic mixture was stirred for 10 min. The layers were separated. The organic layer was washed with aqueous NH$_4$OAc (10 vol, 50 mL). After stirring for 10 min, the layers were separated. The combined aqueous layers were washed with DCM (5 vol). The combined organic streams were solvent swapped into MTBE (2×10 vol MTBE) on a rotary evaporator to a final volume of about 10 vol MTBE. To this was added DARCO™ G60 activated charcoal (50 wt %, 2.5 g) and stirred for 30 min at RT. The charcoal was removed by filtration through a pad of CELITE™ and washed with MTBE (30-40 vol). The resulting MTBE stream was concentrated on the rotary evaporator to a final volume of 25 vol MTBE. To this stirred reaction stream was added anhydrous HCl (2 eq, 3M in CPME) over 30 min. The resulting slurry was stirred for at least 12 h at RT under N$_2$. The slurry was filtered and washed with MTBE (5 vol). The isolated solid was dried at 40° C. under vacuum for NLT 4 h to afford the HCl salt of compound 27a (4.7 g, 82% yield) as an off-white powder. HRMS M/Z Expected: 538.32; Found: (M+H) 539.3262.

Example 8—Fragment B1

Figure 3B:
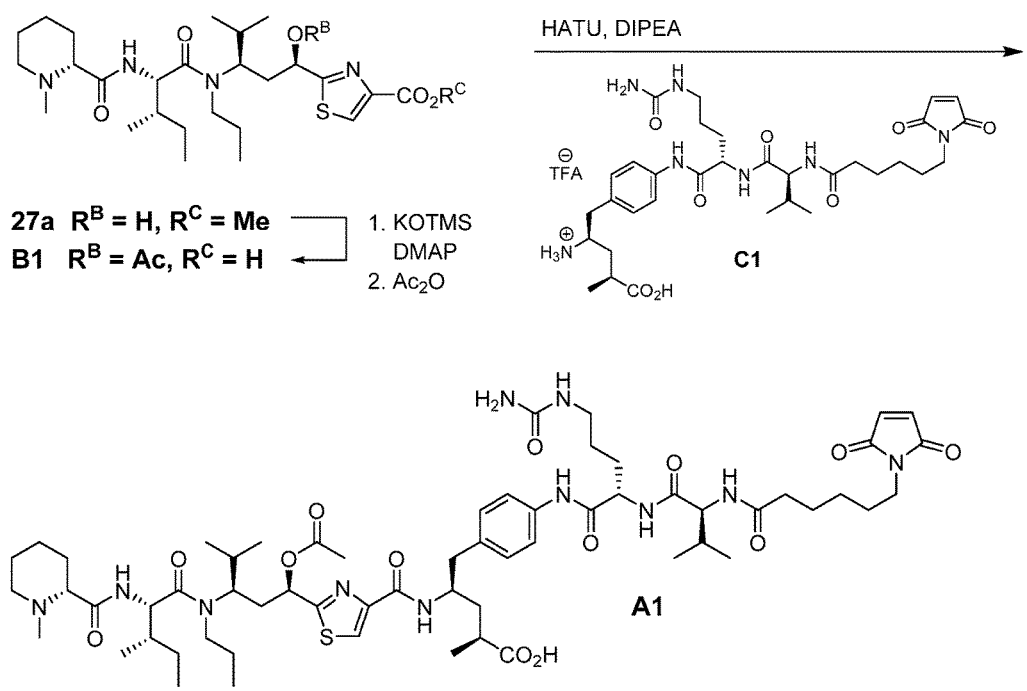

This example relates to the synthesis of fragment B1 (FIG. 3B).

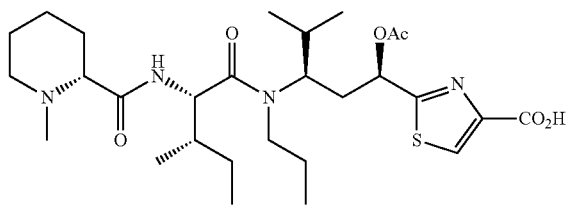

B1

Compound 27a (1.0 equiv.) and 2-MeTHF (12.0 vol) were added to a 50 mL RB at 20° C. Potassium trimethylsilanoate (KOTMS, 5.0 equiv.) was added. The reaction mixture was stirred for 1 h at 20° C. A sample was taken and reaction conversion was determined by HPLC analysis. 4-(Dimethylamino)pyridine (DMAP, 1.0 equiv.) was added followed by acetic anhydride (6.0 equiv.). After stirring at RT for 1 h, a sample was take and reaction conversion determined by HPLC analysis. The resulting slurry (KOAc precipitate) was filter to remove KOAc salt. The filter cake was washed with 2-MeTHF. Water (8 vol) was added to the filtrate, followed by trifluoroacetic acid (TFA) to adjust the pH to 2-3. The aqueous and organic layers were separated. The aqueous layer was washed with 2-MeTHF (4 vol). The organic phases were combined and to them was added an additional 1 equiv. TFA. The mixture was azeotroped with toluene to remove water and 2-MeTHF. The resulting residue was diluted with a minimum volume of toluene and stirred at RT. MTBE was added (10 vol) and the mixture was seeded with a small amount of compound B1 from an earlier preparation. The product began to crystallize slowly. After stirring at RT for at least 12 h, compound B1 was isolated by filtration. The filter cake was washed with MTBE (2×3 vol). The product was dried in a vacuum oven (40° C.) for 24-48 h. HRMS M/Z Expected: 567.3211; Found: (M+H) 567.3195; yield 82%.

Fragment B1 can be coupled with a fragment C comprising a Tup subunit (or analog thereof) and a linker moiety to make an analog-linker compound usable for the preparation of an antibody-drug conjugate. Or, where the desired product is a tubulysin analog without a linker attached, fragment B1 can be coupled with a Tup subunit or analog thereof to make such analog.

Analog/linker compound A1 can be made by coupling fragments B1 and C1, as shown in FIG. 3B by following the procedure of Cheng et al. 2013.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.
Cheng et al., U.S. Pat. No. 8,394,922 B2 (2013).
Cong et al., U.S. Pat. No. 8,980,824 B2 (2015).
Domling et al., U.S. Pat. No. 7,816,377 B2 (2010).
Hamel et al., *Curr. Med. Chem.—Anti-Cancer Agents* 2002, 2, 19.
Kazmaier et al., *Open Nat. Prod. J.* 2013, 6, 12.
Khalil et al., *ChemBioChem* 2006, 7, 678.
Li et al., *Org. Lett.* 2012, 14 (1), 214.
Lipschutz et al., *Angew. Chem. Int. Ed.* 2008, 47, 10183.
Park et al., *SynLett* 2015, 26, 1063.
Perez et al., U.S. application Ser. No. 14/833,422, filed 24 Aug. 2015.
Richter, U.S. Pat. No. 8,980,833 B2 (2015).
Rooke et al., *J. Am. Chem. Soc.* 2010, 132, 11926.
Rooke et al., *Org. Lett.* 2012, 14 (13), 3328.
Rooke et al., *Tetrahedron* 2014, 70, 4232.
Sani et al., *Angew. Chem. Int. Ed.* 2007, 46, 3526.
Schrama et al., *Nature Rev. Drug Disc.* 2006, 5, 147.
Shi et al., *Nature Chem.* 2015, 7, 38.
Shibue et al., *Chem. Eur. J.* 2010, 16, 11678.
Sumida et al., *Org. Lett.* 2012, 14 (6), 1552.
Wipf et al., US 2010/0047841 A1 (2010).
Yang et al., *Chem. Asian J.* 2013, 8, 1213.
Zanda et al., U.S. Pat. No. 8,580,820 B2 (2013).

What is claimed is:

1. A process for making a compound 21, or a salt thereof

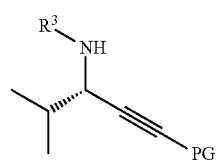

21 comprising the steps of
(a) combining a compound 18

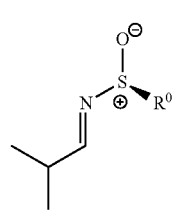

18 with a compound 19

Li—≡—PG    19 in a reaction medium and allowing the two compounds to react with each other;
(b) then adding to the reaction medium a compound 20

$R^3$—$X^1$    20

(c) then adding a de-chelating agent to the reaction medium to produce a compound 21; and
(d) optionally adding a primary or secondary alcohol and an anion source to the reaction medium to produce a salt of compound 21;
wherein
$R^0$ is $C_1$-$C_4$ alkyl;
$R^3$ is Me, Et, or n-Pr;
$X^1$ is Cl, Br, I triflate, mesylate, or tosylate; and
PG is a silyl protective group.

2. A process according to claim 1, wherein
$R^3$ is n-Pr, $X^1$ is Br,
the de-chelating agent is DMF, and
PG is triisopropyl silyl.

3. A process according to claim 2, wherein compound 18 has a structure represented by formula 18a:

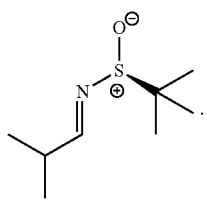

18a

4. A process for making a compound 23

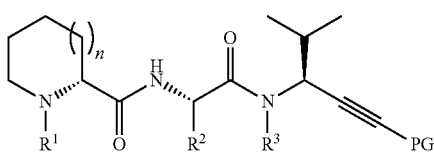

23 comprising reacting a compound 21

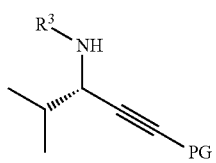

21 with a compound 22

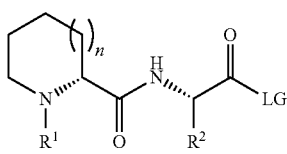

22 in the presence of a haloalkyl aluminum compound to form compound 23;
wherein
n is 0, 1, or 2;
$R^1$ is H or $C_1$-$C_4$ alkyl;
$R^2$ is Me, Et, n-Pr, i-Pr, or (S) sec-butyl;
$R^3$ is Me, Et, or n-Pr;
PG is a silyl protective group; and
LG is a leaving group.

5. A process according to claim 4, wherein
the haloalkyl aluminum compound is $Al(X^4)_2R^4$ or $Al(R^4)_2X^4$, where $R^4$ is methyl, ethyl, or isobutyl, and $X^4$ is Cl or Br.

6. A process according to claim 4, wherein the haloalkyl aluminum compound is $Et_2AlCl$.

7. A process according to claim 6, wherein
n is 1;
$R^1$ is Me;
$R^2$ is (S) sec-butyl;
$R^3$ is n-Pr;
PG is triisopropyl silyl; and
LG is pentafluorophenoxy.

8. A process for making a compound 26

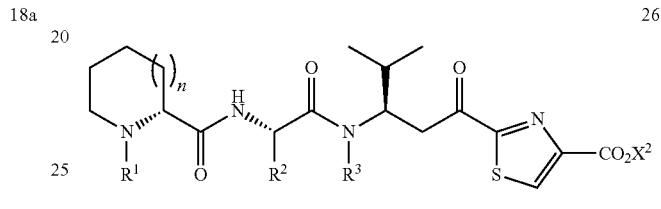

26 comprising regioselectively hydrating a compound having a structure according to formula 25

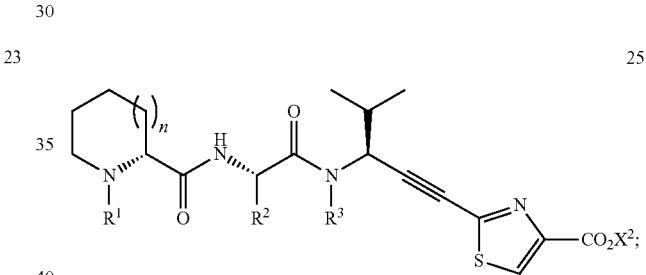

25 wherein
n is 0, 1, or 2;
$R^1$ is H or $C_1$-$C_4$ alkyl;
$R^2$ is Me, Et, n-Pr, i-Pr, or (S) sec-butyl;
$R^3$ is Me, Et, or n-Pr; and
$X^2$ is $C_1$-$C_3$ alkyl, aryl or benzyl; the aryl or benzyl group being optionally substituted with Cl, Br, Me, Et, CN, $NO_2$ or $O(C_1$-$C_3$ alkyl).

9. A method according to claim 8, comprising the steps of
(a) treating compound 25 with a silicon or boron metalating agent in the presence of a metal catalyst selected from the group consisting of a Pd, Pt, Cu, Ru, Rh and Au catalyst, to produce a metalated intermediate; and
(b) oxidizing the metalated intermediate with an oxidizing agent to produce compound 26.

10. A process according to claim 9, wherein
the metal catalyst is tris(dibenzylideneacetone)dipalladium(0),
the metalating agent is $(EtO)_2SiMeH$, and
the oxidizing agent is hydrogen peroxide.

11. A process according to claim 10, wherein
n is 1,
$R^1$ is Me,
$R^2$ is (S) sec-butyl,
$R^3$ is n-Pr, and
$X^2$ is $C_1$-$C_3$ alkyl.

12. A process for making a compound 27

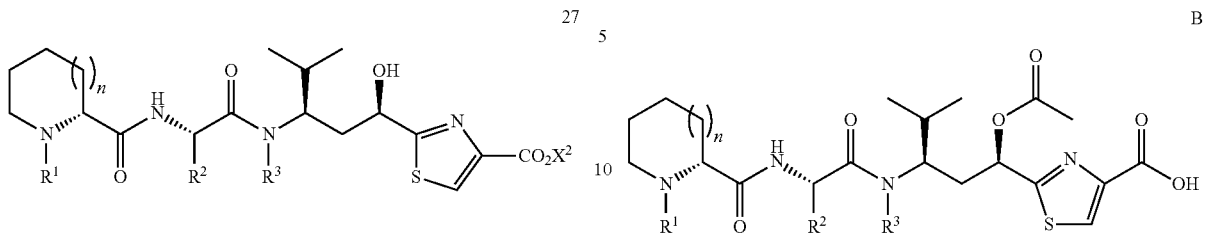

comprising enantioselectively hydrogenating a compound 26

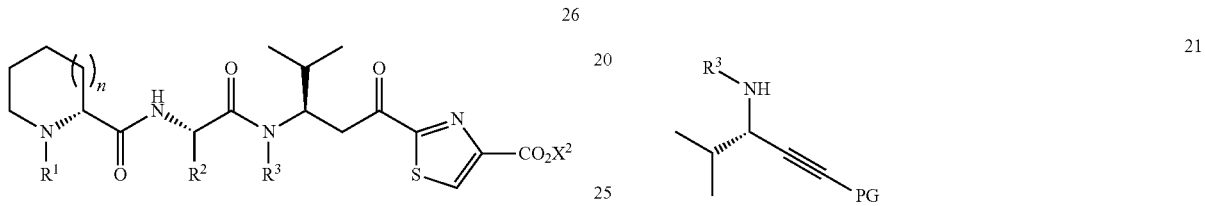

in the presence of an asymmetric hydrogenation catalyst; wherein n is 0, 1, or 2;

$R^1$ is H or $C_1$-$C_4$ alkyl;

$R^2$ is Me, Et, n-Pr, i-Pr, or (S) sec-butyl;

$R^3$ is Me, Et, or n-Pr; and $X^2$ is $C_1$-$C_3$ alkyl, aryl or benzyl; the aryl or benzyl group being optionally substituted with Cl, Br, Me, Et, CN, $NO_2$ or $O(C_1$-$C_3$ alkyl).

13. A process according to claim 12, wherein the asymmetric hydrogenation catalyst is an R,R-Noyori catalyst.

14. A process according to claim 13, wherein the R,R-Noyori catalyst has the structure

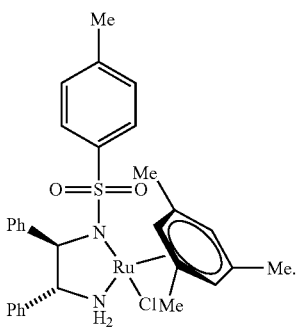

15. A process according to claim 14, wherein n is 1, $R^1$ is Me, $R^2$ is (S) sec-butyl, $R^3$ is n-Pr, and $X^2$ is $C_1$-$C_3$ alkyl.

16. A process for making a compound B,

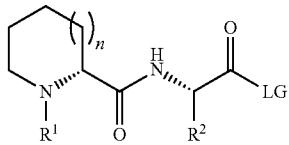

comprising the steps of:

(a) preparing a compound 21 or a salt thereof

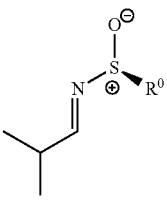

from compounds 18, 19 and 20

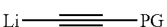

$R^3$—$X^1$;

(b) reacting compound 21 with a compound 22

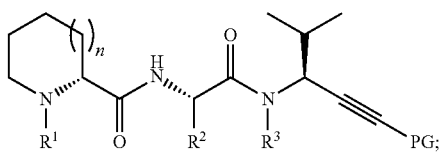

in the presence of a haloalkyl aluminum compound to produce compound 23

(c) removing the group PG from compound 23 to form a compound 23'

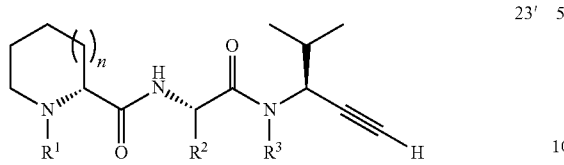

(d) coupling compound 23' and a compound 24

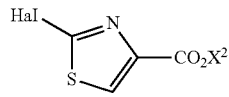

to produce compound 25

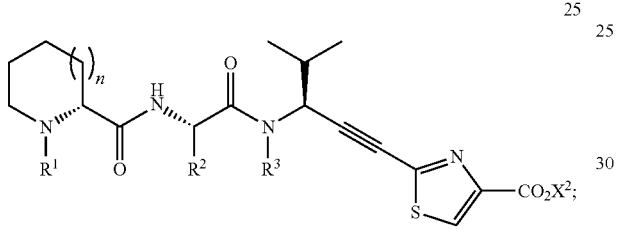

(e) regioselectively hydrating compound 25 to produce a compound 26

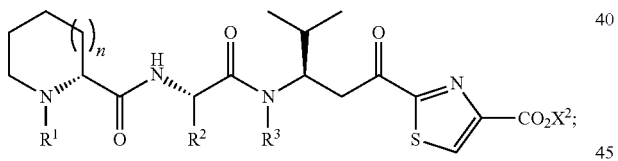

(f) enantioselectively reducing compound 26 to produce a compound 27

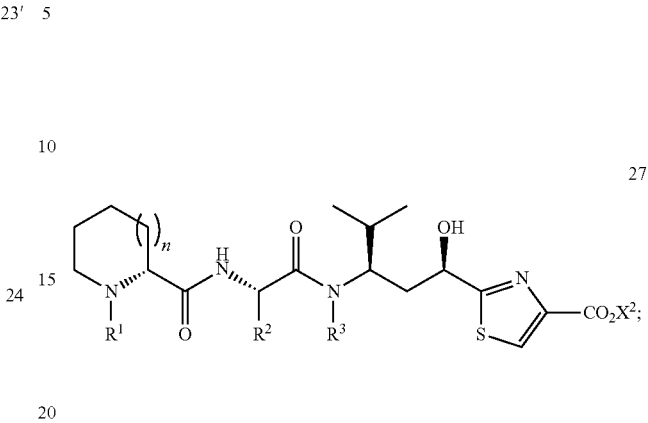

and (g) hydrolyzing the ester group and acetylating the hydroxyl group in compound 27 to produce compound B;

wherein n is 0, 1, or 2;

$R^0$ is $C_1$-$C_4$ alkyl (especially t-butyl);

$R^1$ is H or $C_1$-$C_4$ alkyl;

$R^2$ is Me, Et, n-Pr, i-Pr, or (S) sec-butyl;

$R^3$ is Me, Et, or n-Pr;

$X^1$ is Cl, Br, I, triflate, mesylate, or tosylate;

$X^2$ is $C_1$-$C_3$ alkyl, aryl or benzyl; the aryl or benzyl group being optionally substituted with Cl, Br, Me, Et, CN, $NO_2$ or $O(C_1$-$C_3$ alkyl);

PG is a silyl protective group; and

LG is a leaving group.

* * * * *